US012623053B2

(12) United States Patent
Hutar

(10) Patent No.: US 12,623,053 B2
(45) Date of Patent: May 12, 2026

(54) CATHETER SYSTEMS AND METHODS OF USE

(71) Applicant: Piraeus Medical, Inc., Rochester, MN (US)

(72) Inventor: Jared Hutar, Cromwell, MN (US)

(73) Assignee: Piraeus Medical, Inc., Rochester, MN (US)

( * ) Notice: Subject to any disclaimer, the term of this patent is extended or adjusted under 35 U.S.C. 154(b) by 696 days.

(21) Appl. No.: 18/064,843

(22) Filed: Dec. 12, 2022

(65) Prior Publication Data

US 2023/0181870 A1 Jun. 15, 2023

Related U.S. Application Data

(60) Provisional application No. 63/340,276, filed on May 10, 2022, provisional application No. 63/289,038, filed on Dec. 13, 2021.

(51) Int. Cl.
*A61M 25/00* (2006.01)

(52) U.S. Cl.
CPC ...... *A61M 25/0045* (2013.01); *A61M 25/005* (2013.01); *A61M 2025/0004* (2013.01); *A61M 2025/0047* (2013.01)

(58) Field of Classification Search
CPC ............ A61M 25/0045; A61M 25/005; A61M 2025/0004; A61M 2025/0047
See application file for complete search history.

(56) References Cited

U.S. PATENT DOCUMENTS

| | | | |
|---|---|---|---|
| 6,022,336 | A | 2/2000 | Zadno-Azizi |
| 6,090,099 | A | 7/2000 | Samson et al. |
| 6,287,285 | B1 | 9/2001 | Michal et al. |
| 7,967,789 | B2 | 6/2011 | Solar et al. |
| 8,066,693 | B2 | 11/2011 | Tanghoj et al. |
| 9,821,139 | B2 | 11/2017 | Carleo |
| 9,937,319 | B1 | 4/2018 | Leeflang et al. |
| 10,835,711 | B2 | 11/2020 | Yang et al. |
| 11,020,133 | B2 | 6/2021 | Wilson et al. |
| 11,135,398 | B2 | 10/2021 | Tilson et al. |
| 11,224,450 | B2 | 1/2022 | Chou et al. |

(Continued)

FOREIGN PATENT DOCUMENTS

| | | | |
|---|---|---|---|
| EP | 1635900 | B1 | 4/2009 |
| JP | 2008000287 | A | 1/2008 |
| JP | 2013192885 | A | 9/2013 |

OTHER PUBLICATIONS

Argon Medical Devices—"Promoting Hydrophilic Coating"—Aug. 10, 2020—Available from Internet <URL: https://www.argonmedical. eu.com/articles/promoting-hydrophilic-coating>.

(Continued)

*Primary Examiner* — Dung T Ulsh
(74) *Attorney, Agent, or Firm* — Greenberg Traurig, LLP

(57) ABSTRACT

The disclosure includes a catheter system comprising an inner catheter and an outer catheter configured to at least partially receive the inner catheter. Each of the inner catheter and the outer catheter may comprise an outer surface and an inner surface, wherein each of the outer and inner surfaces may be coated in a hydrophilic coating. In some embodiments, the hydrophilic coating is configured to reduce surface tension and increase lubricity of the inner catheter and the outer catheter.

20 Claims, 18 Drawing Sheets

(56)          References Cited

U.S. PATENT DOCUMENTS

| | | | |
|---|---|---|---|
| 11,395,665 | B2 | 7/2022 | Yang et al. |
| 11,400,255 | B1 | 8/2022 | Chou et al. |
| 2003/0004496 | A1 | 1/2003 | Tanghoj et al. |
| 2006/0240253 | A1 | 10/2006 | Bavaro et al. |
| 2008/0262431 | A1 | 10/2008 | Anderson et al. |
| 2009/0230167 | A1* | 9/2009 | Xiao ..................... A61M 25/04 |
| | | | 227/175.1 |
| 2010/0004607 | A1 | 1/2010 | Wilson et al. |
| 2011/0021994 | A1 | 1/2011 | Anderson et al. |
| 2012/0165790 | A1* | 6/2012 | Gustavsson ............. B65B 53/02 |
| | | | 156/383 |
| 2012/0271281 | A1 | 10/2012 | Schertiger |
| 2014/0081210 | A1 | 3/2014 | Bierman et al. |
| 2014/0224678 | A1 | 8/2014 | Schertiger et al. |
| 2015/0217084 | A1 | 8/2015 | Tassoni et al. |
| 2015/0366462 | A1 | 12/2015 | Ramos et al. |
| 2017/0020540 | A1 | 1/2017 | Chou et al. |
| 2018/0361114 | A1 | 12/2018 | Chou et al. |
| 2019/0247627 | A1 | 8/2019 | Korkuch et al. |
| 2019/0351182 | A1 | 11/2019 | Chou et al. |
| 2019/0366044 | A1 | 12/2019 | Donegan et al. |
| 2020/0038628 | A1* | 2/2020 | Chou ................. A61B 17/1204 |
| 2020/0215259 | A1 | 7/2020 | Leeflang et al. |
| 2020/0289136 | A1 | 9/2020 | Chou et al. |
| 2021/0213250 | A1* | 7/2021 | Chmielewski .... A61M 25/0053 |
| 2021/0252252 | A1 | 8/2021 | Haldis et al. |
| 2021/0378696 | A1 | 12/2021 | Yang et al. |

OTHER PUBLICATIONS

Coatings World—"Lubricious coating technology from Bayer MaterialScience LLC can be applied to inner lumens of catheters"—Mar. 11, 2011—Available from Internet <URL://www.coatingworld.com/issues/2011-03/view_products/lubricious coating-technology-from-bayer-materials/>.
Biocoat—"Hydak Hydrophilic Coatings"—Downloaded Jan. 17, 2023—Available from Internet <URL:https://biocoat.com/hydak/>.

* cited by examiner inner
catheter
26 catheter system 10 hub
54

52
hub 12
outer
catheter 100 catheter system 106 distal end 104 proximal end 108 working lumen 102 outer catheter 110 inner catheter 110 inner catheter 114 distal portion 112 proximal hub 116 distal end 118 pusher wire 122 coil structure 118 pusher wire 110 inner catheter 114 distal portion 112 proximal hub 116 distal end 118 pusher wire 124 braid structure 118 pusher wire 120 hypotube 134 outer surface 132 inner surface 140 lubricious coating 136 heatshrink material 120 hypotube 134 outer surface 132 inner surface 140 lubricious coating 138 reflown polymer 200 catheter system 206 distal end 210 inner catheter 204 proximal end 208 working lumen 202 outer catheter 210 inner catheter 216 hypotube 218 inner surface 220 outer surface 226 lubricious coating 222 heatshrink material 216 hypotube 218 inner surface 220 outer surface 226 lubricious coating 224 reflown polymer

CATHETER SYSTEMS AND METHODS OF USE

CROSS-REFERENCE TO RELATED APPLICATIONS

The entire contents of the following application are incorporated by reference herein: U.S. Provisional Patent Application No. 63/289,038; filed Dec. 13, 2021; and entitled CATHETER SYSTEMS AND METHODS OF USE.

The entire contents of the following application are incorporated by reference herein: U.S. Provisional Patent Application No. 63/340,276; filed May 10, 2022; and entitled CATHETER SYSTEMS AND METHODS OF USE.

SUMMARY

The disclosure includes a catheter system comprising an outer catheter having a proximal end, a distal end located opposite the proximal end, a working lumen extending between the proximal end and the distal end, an outer surface defining an outer diameter, and an inner surface defining an inner diameter. In some embodiments, the catheter system includes an inner catheter having a proximal end, a distal end located opposite the proximal end, a working lumen extending between the proximal end and the distal end, an outer surface defining an outer diameter, and an inner surface defining an inner diameter, wherein the working lumen of the outer catheter is configured to at least partially receive the inner catheter. The catheter system may include a first hydrophilic coating, a second hydrophilic coating, a third hydrophilic coating, and a fourth hydrophilic coating. In some embodiments, the first hydrophilic coating is located on the outer surface of the outer catheter and is configured to reduce surface friction and increase lubricity between the outer surface of the outer catheter and a vessel wall. The second hydrophilic coating may be located on the inner surface of the outer catheter and may be configured to reduce surface friction and increase lubricity between the inner surface of the outer catheter and the outer surface of the inner catheter. In some embodiments, the third hydrophilic coating is located on the outer surface of the inner catheter and configured to reduce surface friction and increase lubricity between the inner surface of the outer catheter and the outer surface of the inner catheter. The fourth hydrophilic coating may be located on the inner surface of the inner catheter and may be configured to reduce surface friction and increase lubricity on the inner surface of the inner catheter.

In some embodiments, the outer catheter comprises a device wall, and the inner catheter comprises a device wall, wherein the device wall of the outer catheter includes at least one polymer coupled to an outer catheter reinforcement structure, and wherein the device wall of the inner catheter includes at least one polymer coupled to an inner catheter reinforcement structure. The outer catheter reinforcement structure may comprise a braid and coil reinforcement structure, and the inner catheter reinforcement structure may comprise a braid and coil reinforcement structure. In some embodiments, the at least one polymer is configured to provide at least one of flexibility and structural support to the outer catheter and the inner catheter. The braid and coil reinforcement structure may comprise a coil defining a pitch smaller than 0.03 inches. The device wall of the outer catheter may be located between the first hydrophilic coating and the second hydrophilic coating, and the device wall of the inner catheter may be located between the third hydrophilic coating and the fourth hydrophilic coating.

The catheter system may comprise a guidewire configured to extend through the inner catheter, wherein the fourth hydrophilic coating may be configured to reduce surface friction and increase lubricity between the guidewire and the inner surface of the inner catheter. In some embodiments, the first hydrophilic coating comprises a substantially smooth surface, and the third hydrophilic coating comprises a substantially smooth surface. The second hydrophilic coating may comprise a textured surface, and the fourth hydrophilic coating may comprise a textured surface.

In some embodiments, the first hydrophilic coating extends between the proximal end and the distal end of the outer catheter. The first hydrophilic coating may extend along a surface extending between the proximal end and the distal end of the outer catheter. In some embodiments, the second hydrophilic coating extends between the proximal end and the distal end of the outer catheter. The second hydrophilic coating may extend along a surface extending between the proximal end and the distal end of the outer catheter. In some embodiments, the third hydrophilic coating extends between the proximal end and the distal end of the outer catheter. The third hydrophilic coating may extend along a surface extending between the proximal end and the distal end of the outer catheter. In some embodiments, the fourth hydrophilic coating extends between the proximal end and the distal end of the outer catheter. The fourth hydrophilic coating may extend along a surface extending between the proximal end and the distal end of the outer catheter.

The catheter system may further comprise an outer reinforcement structure located on the second hydrophilic coating, the outer reinforcement structure configured to provide structural support to the outer catheter, and an inner reinforcement structure located on the fourth hydrophilic coating, the inner reinforcement structure configured to provide structural support to the inner catheter. In some embodiments, the outer reinforcement structure comprises a braid and coil reinforcement structure, and the inner reinforcement structure comprises a braid and coil reinforcement structure. The catheter system may further comprise an outer jacket structure coupled to the outer reinforcement structure, wherein the outer jacket structure may be configured to provide at least one of flexibility and structural support to the outer catheter, and an inner jacket structure coupled to the inner reinforcement structure, wherein the inner jacket structure may be configured provide at least one of flexibility and structural support to the inner catheter. In some embodiments, the outer jacket structure comprises a polymer jacket structure, and the inner jacket structure comprises a polymer jacket structure. The catheter system may further comprise an outer jacket structure coupled to the outer reinforcement structure, wherein the outer jacket structure may be configured to cover the outer reinforcement structure and thereby provide a substantially smooth surface to couple to the first hydrophilic coating, and an inner jacket structure coupled to the inner reinforcement structure, wherein the inner jacket structure may be configured to cover the inner reinforcement structure and thereby provide a substantially smooth surface to couple to the third hydrophilic coating.

In some embodiments, the outer diameter of the outer catheter is about 0.111 inches, and the inner diameter of the outer catheter is about 0.100 inches. The outer diameter of the inner catheter may be about 0.098 inches, and the inner diameter of the inner catheter may be about 0.088 inches.

The disclosure includes a method of using a catheter system, the method comprising inserting an outer catheter into a patient's vasculature, wherein the outer catheter includes a proximal end and a distal end located opposite the proximal end, advancing the outer catheter through the patient's vasculature toward a vascular lesion, and advancing the outer catheter to a location selected from the group consisting of a first location and a second location. In some embodiments, the first location is within a first predetermined distance from the vascular lesion, and the second location is within a second predetermined distance from the vascular lesion. When the outer catheter is in the first location, the outer catheter may be able to aspirate the vascular lesion, and when the outer catheter is in the second location, the outer catheter may be unable to aspirate the vascular lesion. In some embodiments, when the outer catheter is in the first location, the method further comprises aspirating the vascular lesion with the outer catheter. When the outer catheter is in the second location, the method may further comprise advancing an inner catheter through the outer catheter toward the first location. In some embodiments, when the inner catheter is in the first location, the method further comprises aspirating the vascular lesion with the inner catheter.

The disclosure includes a catheter system comprising an outer catheter having a proximal end, a distal end located opposite the proximal end, and a working lumen extending between the proximal end and the distal end. The catheter system may also include an inner catheter having a proximal hub, a distal portion having a distal end located opposite the proximal hub, and a pusher wire extending between the proximal hub and the distal portion. In some embodiments, the working lumen is configured to at least partially receive the inner catheter. The distal portion of the inner catheter may comprise one of a hypotube, a coil structure, and a braid structure. In some embodiments, the hypotube comprises a distal portion and a proximal portion located opposite the distal portion, wherein the proximal portion is configured to taper to a proximal end coupled to the pusher wire. The pusher way may be configured to facilitate navigation of the inner catheter through the working lumen of the outer catheter.

In some embodiments, the hypotube comprises an inner surface and an outer surface. The outer surface may be covered with a heatshrink material. In some embodiments, at least a portion of the heatshrink material and at least a portion of the inner surface of the hypotube are coated with a lubricious coating. The lubricious coating may comprise one of a hydrophilic coating and silicone. In some embodiments, substantially the entirety of the heatshrink material and substantially the entirety of the inner surface of the hypotube are coated with a lubricious coating.

The outer surface may be covered with a reflown polymer material. In some embodiments, at least a portion of the reflown polymer material and at least a portion of the inner surface of the hypotube are coated with a lubricious coating. The lubricious coating may comprise one of a hydrophilic coating and silicone. In some embodiments, substantially the entirety of the reflown polymer material and substantially the entirety of the inner surface of the hypotube are coated with a lubricious coating.

The hypotube may comprise a stainless steel hypotube. In some embodiments, the hypotube comprises a nitinol hypotube. The hypotube may define a length of about twenty centimeters. In some embodiments, the pusher wire comprises a round wire. The pusher wire may comprise a flat wire.

The disclosure includes a catheter system comprising an outer catheter having a proximal end, a distal end located opposite the proximal end, and a working lumen extending between the proximal end and the distal end, and an inner catheter having a proximal end and a distal end located opposite the proximal end, wherein the working lumen is configured to at least partially receive the inner catheter, and wherein the inner catheter comprises a hypotube.

In some embodiments, the hypotube comprises an inner surface and an outer surface. The outer surface may be covered with a heatshrink material. In some embodiments, at least a portion of the heatshrink material and at least a portion of the inner surface of the hypotube are coated with a lubricious coating. The lubricious coating may comprise one of a hydrophilic coating and silicone. In some embodiments, substantially the entirety of the heatshrink material and substantially the entirety of the inner surface of the hypotube are coated with a lubricious coating.

The outer surface may be covered with a reflown polymer material. In some embodiments, at least a portion of the reflown polymer material and at least a portion of the inner surface of the hypotube are coated with a lubricious coating. The lubricious coating may comprise one of a hydrophilic coating and silicone. In some embodiments, substantially the entirety of the reflown polymer material and substantially the entirety of the inner surface of the hypotube are coated with a lubricious coating.

The hypotube may comprise a stainless steel hypotube. In some embodiments, the hypotube comprises a nitinol hypotube.

DETAILED DESCRIPTION

Figure 1:
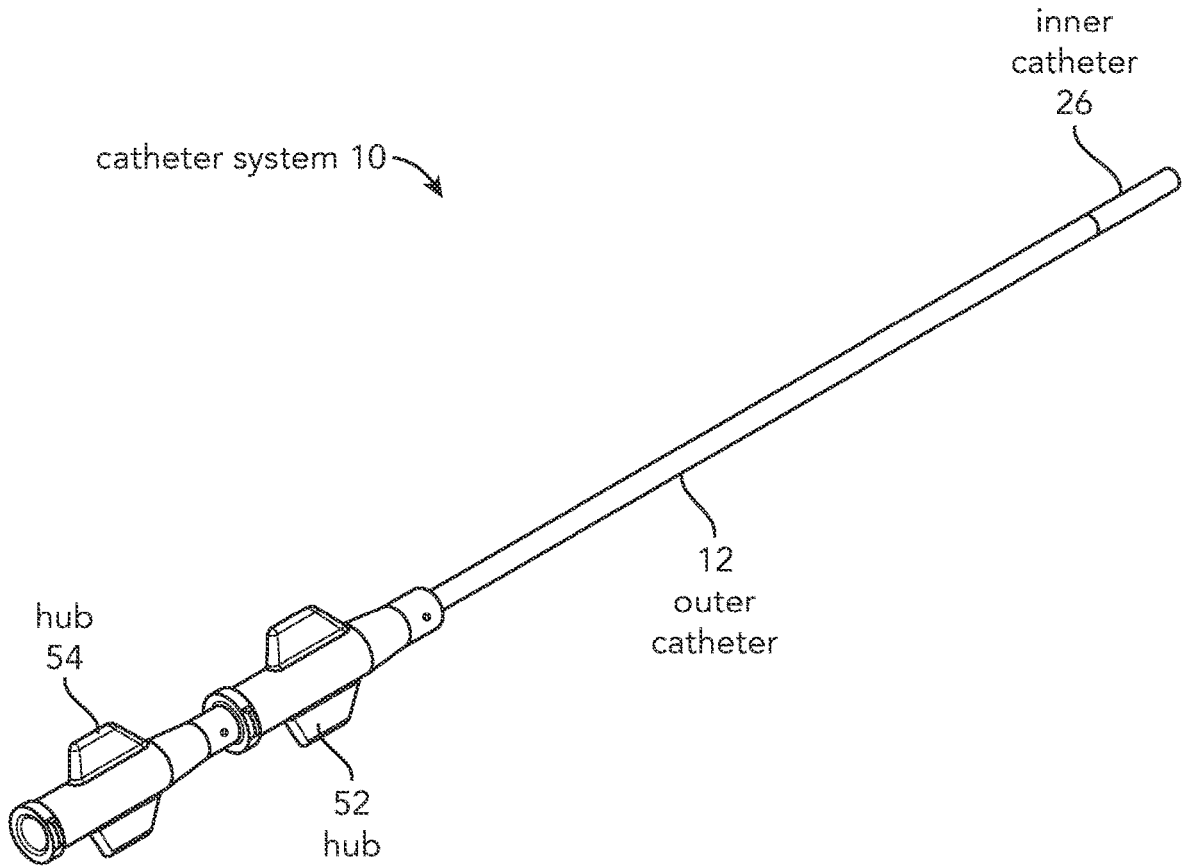
FIG. 1 illustrates a perspective view of a catheter system including an outer catheter and an inner catheter, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order-dependent. Additionally, the structures, systems, and/or devices described herein may be embodied as integrated components or as separate components.

To compare various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The invention generally relates to medical devices and methods of use. Embodiments of the invention include devices and methods for performing thrombectomy or embolectomy in a patient. Acute Ischemic Stroke (AIS) can be caused by thrombus, embolus, or other occlusions in regions of the internal carotid artery (ICA) such as the Petrous part, Cavernous part, or Cerebral part. Approaches for performing thrombectomy or embolectomy to treat AIS include positioning a device—such as an aspiration catheter, a balloon guiding catheter, or other devices—in the carotid artery at a location upstream from the occlusion, typically at a proximal location in the artery such as the cervical part. Navigation to the proximal location can be difficult due to the tortuous nature and small vessel size of the vasculature usually involved in an AIS.

Traditional approaches for treating AIS and lesions in other areas of the body involve the use of several devices of varying sizes and stiffnesses to strike the right balance of size and flexibility for navigation, trackability, and aspiration power. As a result, thrombectomy procedures can take a more significant amount of time as the physician uses trial and error to determine which device/combination of devices will reach and remove the occlusion. In a situation where "time is brain," reducing the amount of time required to remove the thrombus, embolus, or other occlusion is crucial to achieving the best possible outcome for the patient.

There is a continuing need for improved devices and methods for mechanical revascularization such as thrombectomy and embolectomy in the ICA and other vasculature.

In particular, there is a need for devices and methods that provide enhanced efficacy and efficiency of treatment.

Component Index

10—catheter system
12—outer catheter
14—proximal end (outer catheter)
16—distal end (outer catheter)
18—outer surface (outer catheter)
20—inner surface (outer catheter)
22—outer diameter (outer catheter)
24—inner diameter (outer catheter)
26—inner catheter
28—proximal end (inner catheter)
30—distal end (inner catheter)
32—outer surface (inner catheter)
34—inner surface (inner catheter)
36—outer diameter (inner catheter)
38—inner diameter (inner catheter)
40$a$—first hydrophilic coating
40$b$—second hydrophilic coating
40$c$—third hydrophilic coating
40$d$—fourth hydrophilic coating
42—device wall of the outer catheter
44—device wall of the inner catheter
46—at least one polymer
48—outer catheter reinforcement structure
50—inner catheter reinforcement structure
52—hub (outer catheter)
54—hub (inner catheter)
100—catheter system
102—outer catheter
104—proximal end (outer catheter)
106—distal end (outer catheter)
108—working lumen
110—inner catheter
112—proximal hub (inner catheter)
114—distal portion (inner catheter)
116—distal end (inner catheter)
118—pusher wire
120—hypotube
122—coil structure
124—braid structure
126—distal portion (hypotube)
128—proximal portion (hypotube)
130—proximal end (hypotube)
132—inner surface (hypotube)
134—outer surface (hypotube)
136—heatshrink material
138—reflown polymer
140—lubricious coating
200—catheter system
202—outer catheter
204—proximal end (outer catheter)
206—distal end (outer catheter)
208—working lumen (outer catheter)
210—inner catheter
212—proximal end (inner catheter)
214—distal end (inner catheter)
216—hypotube
218—inner surface (hypotube)
220—outer surface (hypotube)
222—heatshrink material
224—reflown polymer
226—lubricious coating FIG. 1 illustrates a perspective view of a catheter system 10, according to some embodiments. The catheter system may include an outer catheter 12 and an inner catheter 26, as illustrated in FIG. 1. In some embodiments, the outer catheter 12 includes a hub 52, and the inner catheter 26 includes a hub 54. The catheter system 10 will be described in greater detail throughout this disclosure.

Figure 2A:
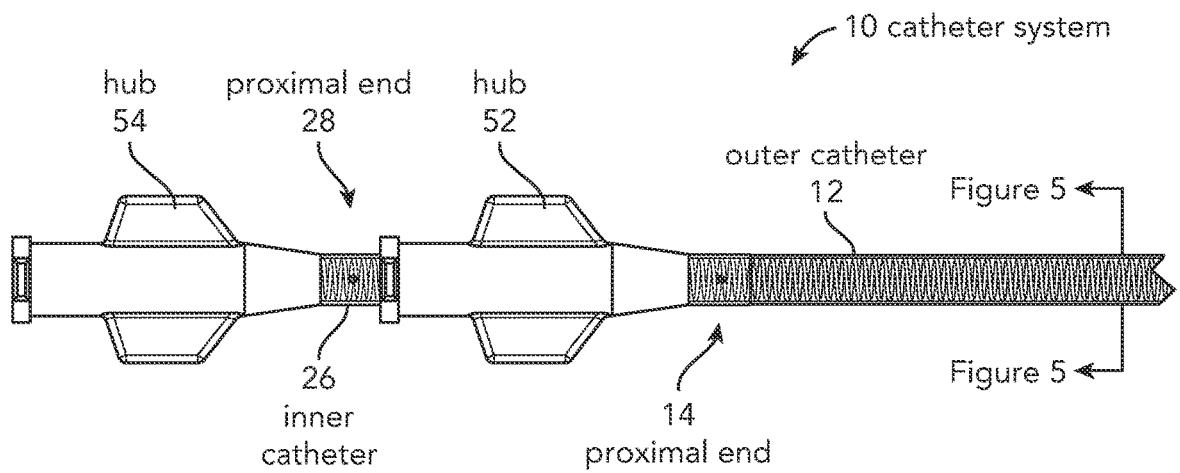
FIGS. 2A and 2B illustrate a catheter system including an outer catheter and an inner catheter, according to some embodiments.
Figure 2B:
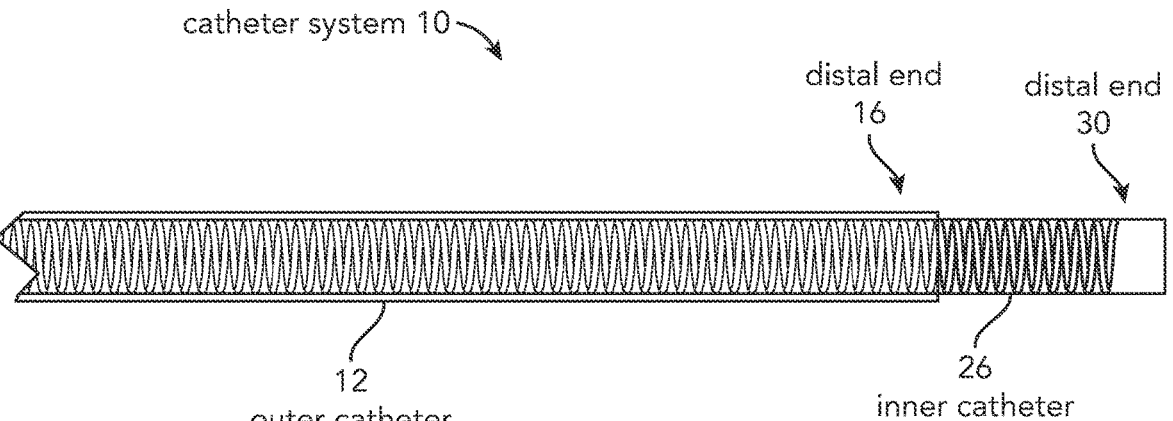

FIGS. 2A and 2B illustrate the catheter system 10 of FIG. 1 in greater detail. As shown in FIG. 2A, the hub 52 of the outer catheter 12 may be located at the proximal end 14 of the outer catheter 12, and the hub 54 of the inner catheter 26 may be located at the proximal end 28 of the inner catheter 26. In some embodiments, the outer catheter 12 includes a distal end 16 located opposite the proximal end 14, and the inner catheter 26 includes a distal end 30 located opposite the proximal end 28.

The outer catheter 12 may be sized and configured to at least partially receive the inner catheter 26, as illustrated in FIGS. 2A and 2B. In some embodiments, the working lumen of the outer catheter 12 is configured to at least partially receive the inner catheter 26. The outer catheter 12 may also be sized and configured to receive other devices, such as a guidewire, a microcatheter, an intermediate catheter, and/or a stent retriever, to name a few non-limiting examples. Accordingly, the catheter system 10 may be thought of as a combination of an inner and outer device (i.e., the inner and outer catheters 26, 12) that can be used concentrically with the inner inside of the outer. In some embodiments, the outer and/or inner catheters 12, 26 can be used individually. For example, during a procedure, such as a thrombectomy, the outer catheter 12 may be inserted into the patient first in an initial attempt to track the outer catheter 12 distally within the anatomy to a surface of a clot. If the outer catheter 12 successfully tracks the surface of the clot, an aspiration force may be applied to the outer catheter 12, thereby removing the clot through the outer catheter 12. If the outer catheter 12 is unsuccessful in tracking to the surface of the clot, the outer catheter 12 may still serve as a guide or support catheter to help deliver the inner catheter 26 through the outer catheter 12 to the surface of the clot.

The possibility of using only a single device (i.e., the outer catheter 12) to remove the clot allows for procedures to be more efficient than current procedure practices, which often involve several steps of introducing and removing several devices. The catheter system 10, including the inner catheter 26 and outer catheter 12, allows for patient anatomy to drive the procedure, rather than following the same steps for every patient, as is the current practice.

Figure 3:
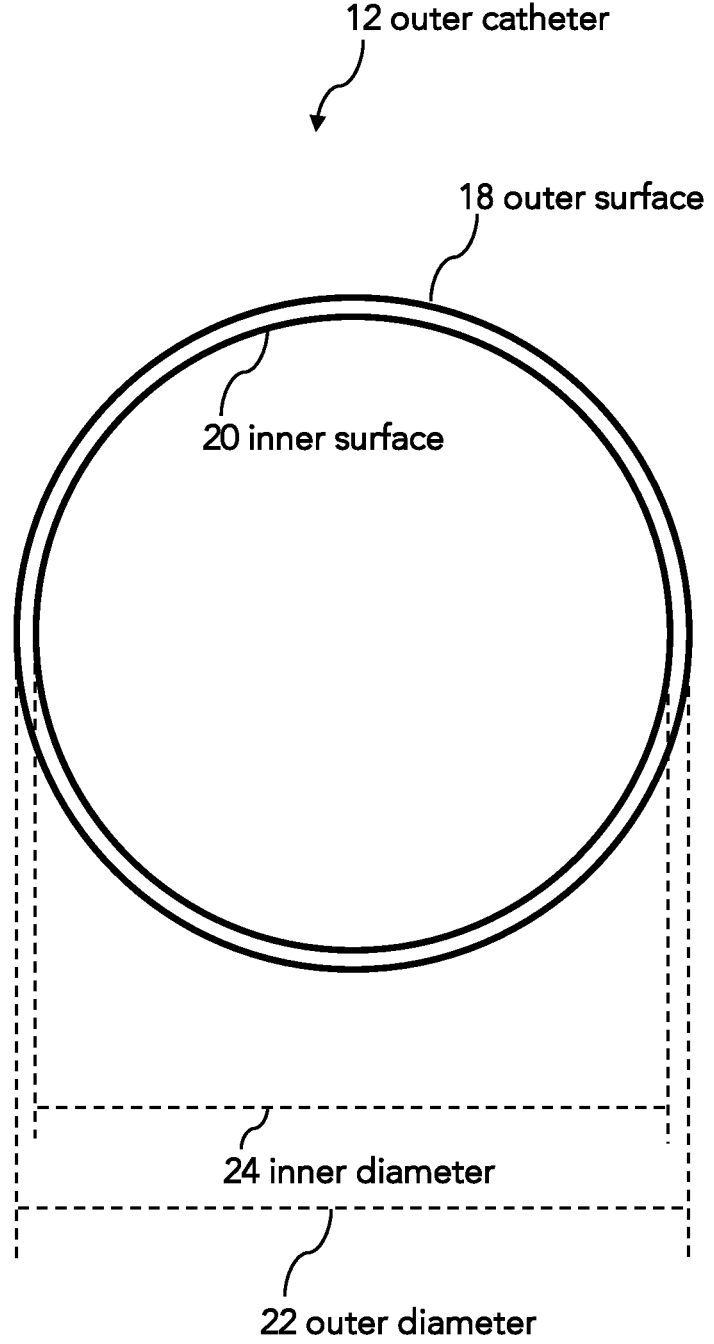
FIG. 3 illustrates a cross-section of an outer catheter, according to some embodiments.
Figure 4:
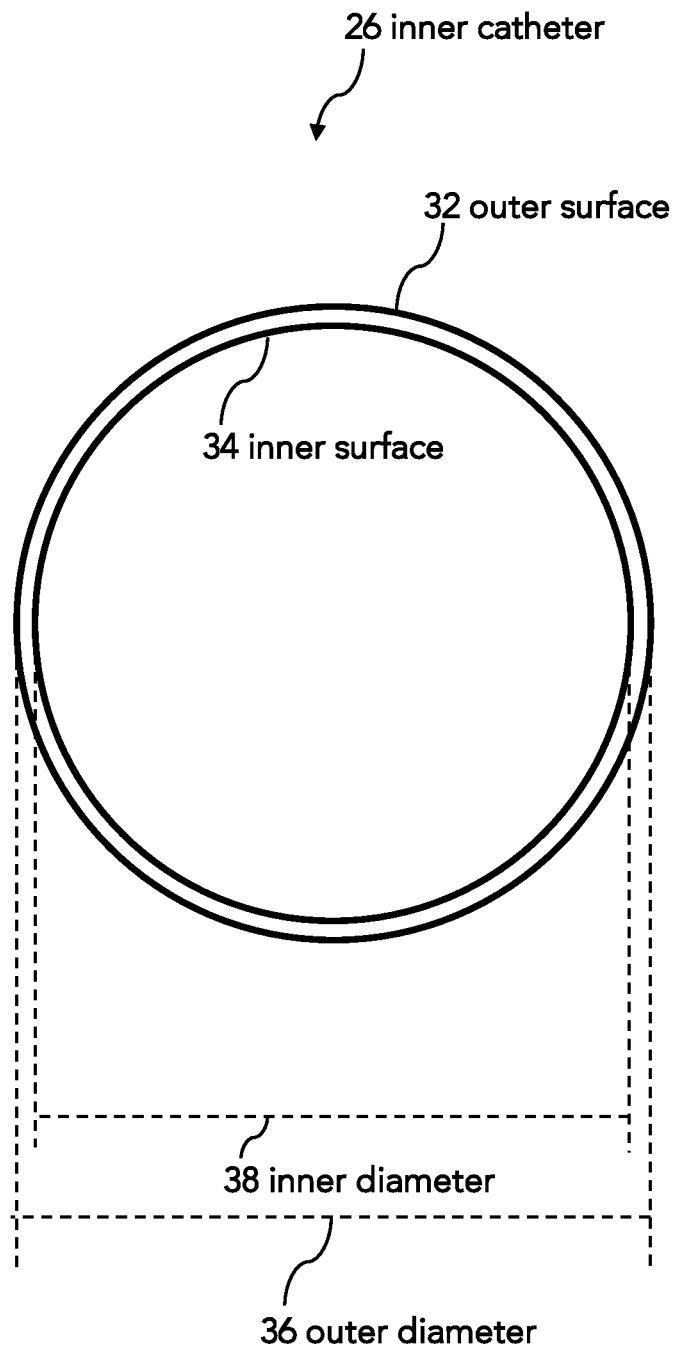
FIG. 4 illustrates a cross-section of an inner catheter, according to some embodiments.

FIGS. 3 and 4 illustrate cross-section views of the outer catheter 12 and inner catheter 26, respectively. Concerning FIG. 3, the outer catheter 12 may include an outer surface 18 defining an outer diameter 22 and an inner surface 20 defining an inner diameter 24. The outer diameter 22 and inner diameter 24 may each define a broad range of dimensions, including, for example, 0.111 inches for the outer diameter 22 and 0.100 inches for the inner diameter 24. As illustrated in FIG. 4, the inner catheter 26 may also include an outer surface 32 defining an outer diameter 36 and an inner surface 34 defining an inner diameter 38. In some embodiments, the outer diameter 36 of the outer surface 32 defines a measurement of 0.098 inches, and the inner diameter 38 of the inner surface 34 defines a measurement of 0.088 inches. It should be noted that the dimensions listed here, for both the outer catheter 12 and the inner catheter 26, are included as non-limiting examples. The outer catheter 12 and inner catheter 26 may both define a wide range of dimensions not explicitly listed in this disclosure.

Figure 5:
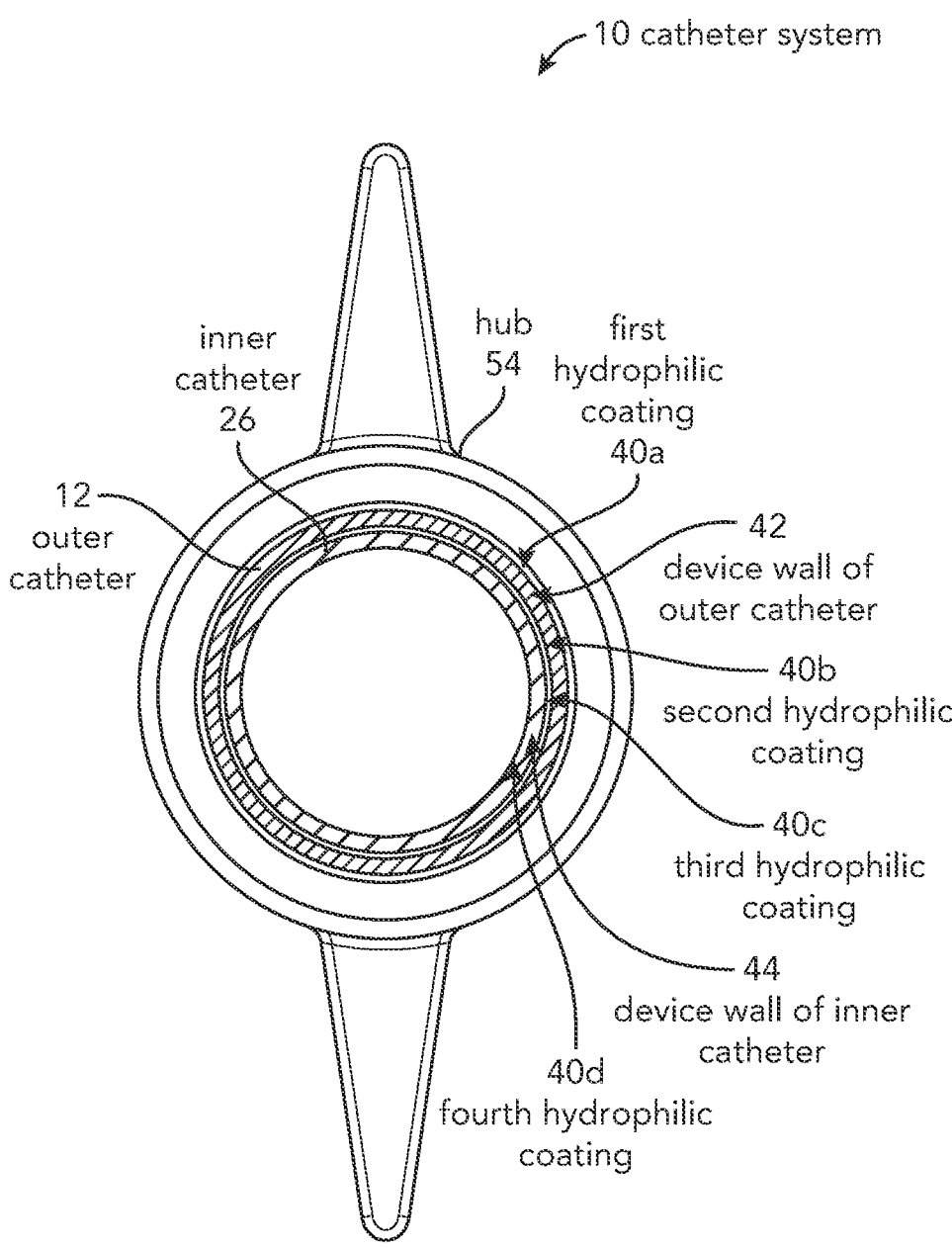
FIG. 5 illustrates a cross-section of a catheter system, including an outer catheter and an inner catheter, according to some embodiments.

As indicated in FIG. 2A, FIG. 5 illustrates a cross-section of the catheter system 10, including both the outer catheter 12 and inner catheter 26, as well as the hub 54 of the inner catheter 26. In some embodiments, as shown in FIG. 5, the outer catheter 12 comprises a device wall of the outer catheter 42, and the inner catheter 26 comprises a device wall of the inner catheter 44. The device walls 42, 44 will be discussed further with reference to FIGS. 6 and 7. The catheter system 10 may also include a first hydrophilic coating 40a, a second hydrophilic coating 40b, a third hydrophilic coating 40c, and a fourth hydrophilic coating 40d, as shown in FIG. 5.

In some embodiments, the first hydrophilic coating 40a is located on the outer surface 18 of the outer catheter 12, and the second hydrophilic coating 40b is located on the inner surface 20 of the outer catheter 12. As such, the device wall of the outer catheter 42 may be located between the first hydrophilic coating 40a and the second hydrophilic coating 40b. Similarly, the third hydrophilic coating 40c may be located on the outer surface 32 of the inner catheter 26, and the fourth hydrophilic coating 40d may be located on the inner surface 34 of the inner catheter 26. In some embodiments, the device wall of the inner catheter 44 is located between the third hydrophilic coating 40c and the fourth hydrophilic coating 40d. Each of the first, second, third, and fourth hydrophilic coatings 40a-d may extend along a surface extending between the proximal ends 14, 28 and distal ends 16, 30 of the outer and inner catheters 12, 26. In some embodiments, the surface extends substantially an entire length of the catheters 12, 26. The surface may extend less than a full length, such as 50%, 25%, or 10% of the entire length. In some embodiments, each of the hydrophilic coatings 40a-d may be configured to cover a distalmost portion, such as 15 centimeters, of the outer and inner catheters 12, 26. It should be noted that each of the hydrophilic coatings 40a-d may be configured to cover any size portion of the catheters 12, 26. It should also be noted that each of the hydrophilic coatings 40a-d does not necessarily define the same length, though they may each define the same length.

Each of the first hydrophilic coating 40a, second hydrophilic coating 40b, third hydrophilic coating 40c, and fourth hydrophilic coating 40d may comprise the same material and thickness. In some embodiments, the thickness of each hydrophilic coating 40a-d is between 0.0001 and 0.001 inches. It should be noted that the term "hydrophilic coating" is used to refer to any general type of lubricious coating that reduces friction and increases trackability of the outer and inner catheters 12, 26, including hydrophilic coatings, silicone coatings, PTFE dust, and any other suitable lubricants. The hydrophilic coating may comprise HYDAK®, produced by Biocoat® Inc. In some embodiments, the hydrophilic coating 40a-d allows the device walls 42, 44 to be thinner than traditional device walls while also improving the performance of the catheters 12, 26. The device walls 42, 44 may define a thickness between 0.001 and 0.04 inches.

Figure 6:
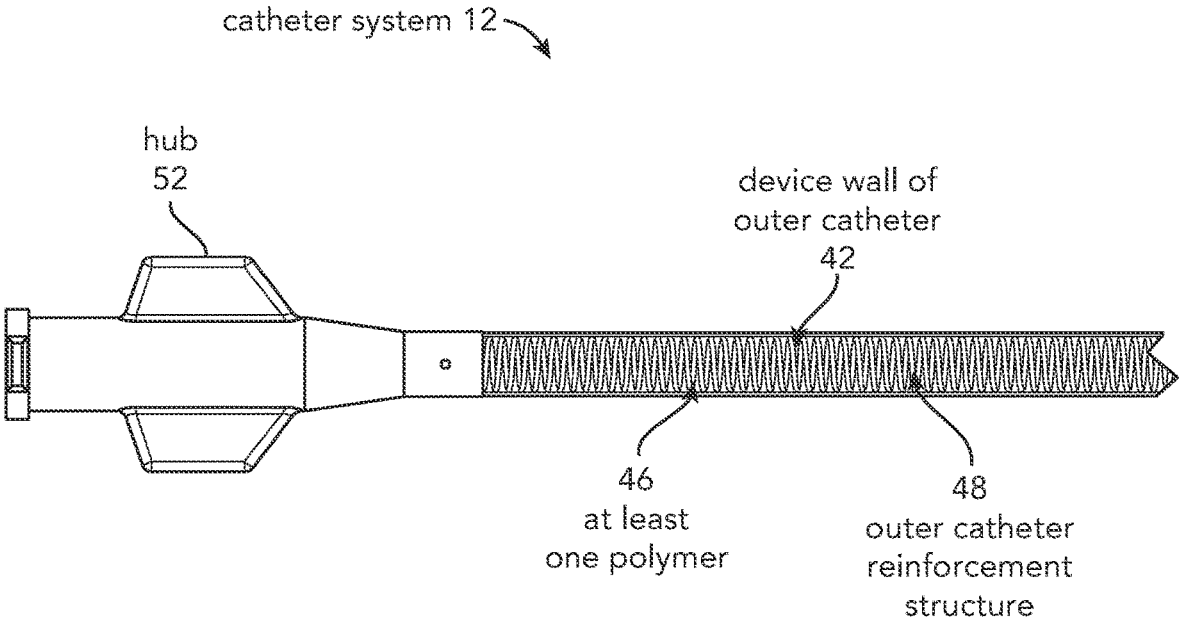
FIG. 6 illustrates an outer catheter, according to some embodiments.

Referring now to FIG. 6, the outer catheter 12 is shown. As previously discussed, the outer catheter 12 may define a device wall 42. In some embodiments, as illustrated in FIG. 6, the device wall 42 comprises at least one polymer 46 and an outer catheter reinforcement structure 48. It should be noted that the at least one polymer 46 may also be referred to as a "polymer jacket structure." The outer catheter reinforcement structure 48 may comprise a metallic braid and coil structure, with the at least one polymer 46 filling any space within the braid and coil structure. The at least one polymer 46 may also cover the outer catheter reinforcement structure 48. In general, the device wall 42 may be thought of as similar to the structure of a garden hose, with a layer of hydrophilic coating 40a, 40b on the inner and outer surfaces of the device wall 42. In some embodiments, the outer catheter reinforcement structure 48 is configured to provide stiffness to a proximal portion of the outer catheter 12 and flexibility to a distal portion of the outer catheter 12. Accordingly, the amount, coil tightness, and/or composition of the outer catheter reinforcement structure 48 may vary depending on the location along the length of the outer catheter 12.

Figure 7:
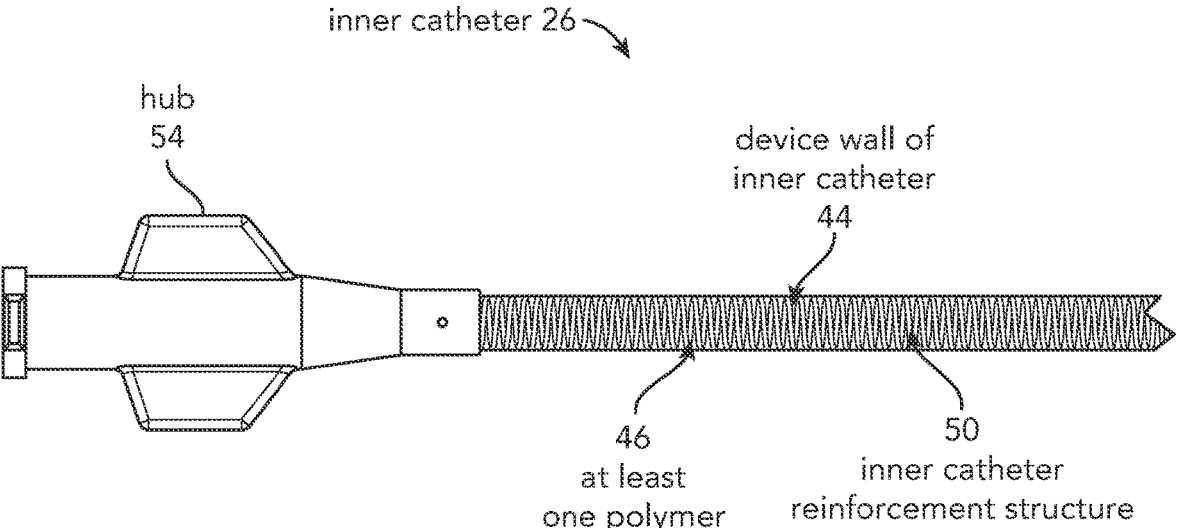
FIG. 7 illustrates an inner catheter, according to some embodiments.

Similar to FIG. 6, FIG. 7 shows the inner catheter 26 including the device wall 44 comprising the at least one polymer 46 and the inner catheter reinforcement structure 50. In some embodiments, the inner catheter reinforcement structure 50 is substantially similar to the outer catheter reinforcement structure 48, including the garden-hose-like structure immersed in the at least one polymer 46. In some embodiments, the inner catheter reinforcement structure 50 is configured to provide stiffness to a proximal portion of the inner catheter 26, and flexibility to a distal portion of the inner catheter 26. Accordingly, the amount, coil tightness, and/or composition of the inner catheter reinforcement structure 50 may vary depending on the location along the length of the inner catheter 26. The device wall of the outer catheter 42 and the device wall of the inner catheter 44 may be substantially the same and may comprise the same type of polymer(s) in the at least one polymer 46, as well as the same type of braid and coil structure in the outer catheter reinforcement structure 48 and inner catheter reinforcement structure 50. The inner catheter 26 may be considered a scaled-down version of the outer catheter 12, with the same elements but smaller dimensions.

Figure 8:
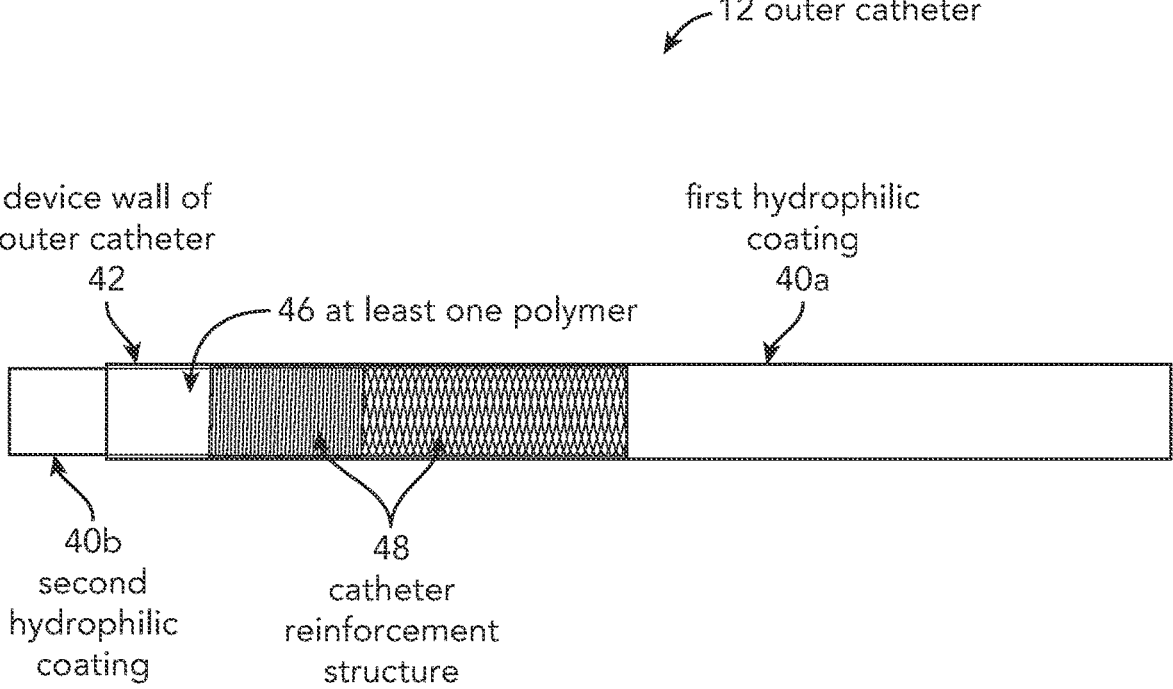
FIG. 8 illustrates an outer catheter including various elements, according to some embodiments.

FIG. 8 is also similar to FIG. 6 in that it illustrates another view of the outer catheter 12, including the various layers of materials. Included in FIG. 8 are the first hydrophilic coating 40a, the second hydrophilic coating 40b, the device wall 42, the at least one polymer 46, and the outer catheter reinforcement structure 48. As discussed with reference to FIG. 6, the device wall 42 may have a structure similar to that of a garden hose, where the at least one polymer 46 and the outer catheter reinforcement structure 48 meld together, with the first hydrophilic coating 40a located on the outer surface and the second hydrophilic coating 40b located on the inner surface.

In some embodiments, the device wall 42 has a "sandwich" structure comprising two layers of the at least one polymer 46, with the outer catheter reinforcement structure 48 between the polymer layers 46. As previously discussed, the outer catheter reinforcement structure 48 may comprise a braid and coil structure. The outer catheter reinforcement structure 48 may include individual coil and braid structures, as indicated by the different appearances of the outer catheter reinforcement structure 48 in FIG. 8. For example, the coil structure may be represented by the portion of the outer catheter reinforcement structure 48 to the left in FIG. 8, while the braid structure may be represented by the portion of the outer catheter reinforcement structure 48 to the right in FIG. 8. In some embodiments, the "sandwich" style device wall 42 comprises an inner layer of at least one polymer 46, the coil structure on top of the inner polymer layer, the braid structure on top of the coil structure, and an outer layer of at least one polymer 46. In the "sandwich" style, the device wall 42 may also include the first hydrophilic coating 40a and the second hydrophilic coating 40b.

In some embodiments, the "sandwich" style device wall 42 allows for a more open coil pitch in the coil structure, thereby enabling the outer catheter 12 to be softer than an embodiment where the coil structure has a tighter or more closed pitch. A softer and more flexible outer catheter 12 can be desirable for certain uses, such as when navigating tortuous anatomy, to give the user (i.e., a medical practitioner) more freedom to move the device at different angles. This "sandwich" style may also provide benefits from a manufacturing standpoint, as a more open coil pitch may be easier to produce with a larger margin of error than a closed pitch.

However, there may also be benefits to a device wall 42 comprising a tighter pitch coil structure. For example, in an embodiment where the outer catheter reinforcement structure 48 includes a coil defining a pitch smaller than 0.03 inches, the second hydrophilic coating 40b may be provided with a substantially solid and ribbed surface to adhere to. In this sense, the second hydrophilic coating 40b (as well as the fourth hydrophilic coating 40d of the inner catheter 26) may be thought of as having a textured, or "ribbed," surface. In comparison, the first hydrophilic coating 40a (and the third hydrophilic coating 40c) may be thought of as having a substantially smooth surface.

In some embodiments, to ensure a sufficiently solid inner surface 20 of the outer catheter 12, the coil comprises a 0.002 inch round coil with a 0.004 inch pitch. A tighter pitch coil may be better for facilitating lubricity of the inner surface 20 of the outer catheter 12. In some embodiments, a coil with a pitch less than 0.025 inches is desirable. A sufficiently tight-pitch coil in the outer catheter reinforcement structure 48, combined with the second hydrophilic coating 40b on the inner surface 20 of the outer catheter 12, may provide enough lubricity to replace the need for a liner, such as a PTFE liner, which is traditionally used in catheter construction.

Regardless of the "style" of device wall 42 used (e.g., "sandwich" or tight-pitch coil), the use of a first and second hydrophilic coating 40a, 40b on the outer catheter 12 may allow for a thinner, more flexible device wall 42, as compared to other types of catheter walls without inner and outer coatings. It should be noted that though FIG. 8 specifically labels the catheter as the outer catheter 12, the layers shown in FIG. 8 and the preceding discussion also apply to the inner catheter 26, such that FIG. 8 may be considered as depicting either the outer catheter 12 or the inner catheter 26.

Figure 9:
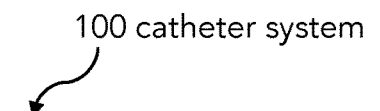
FIG. 9 illustrates a catheter system including an outer catheter and an inner catheter, according to some embodiments.
Figure 9:
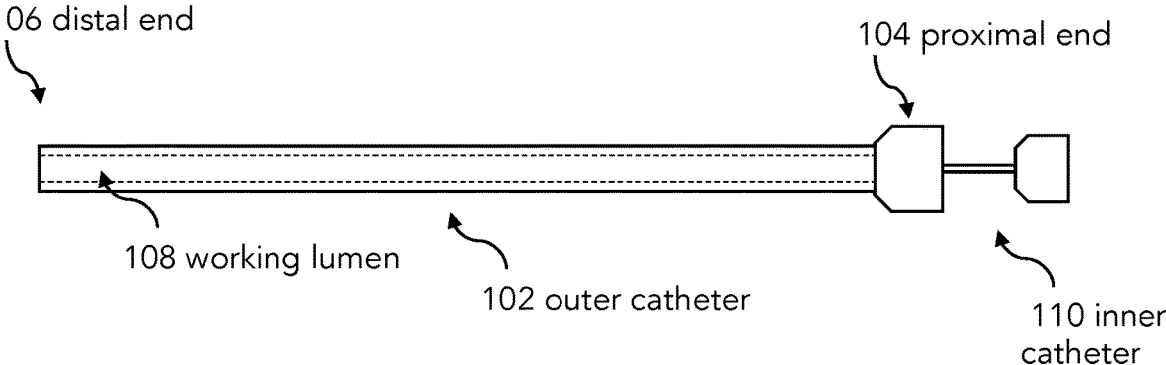

FIG. 9 illustrates a catheter system 100 comprising an outer catheter 102 and an inner catheter 110. As shown, the outer catheter 102 may include a proximal end 104 and a distal end 106 located opposite the proximal end 104. In some embodiments, the outer catheter 102 includes a working lumen 108 extending between the proximal end 104 and the distal end 106. The working lumen 108 may be configured to at least partially receive the inner catheter 110.

Figure 10:
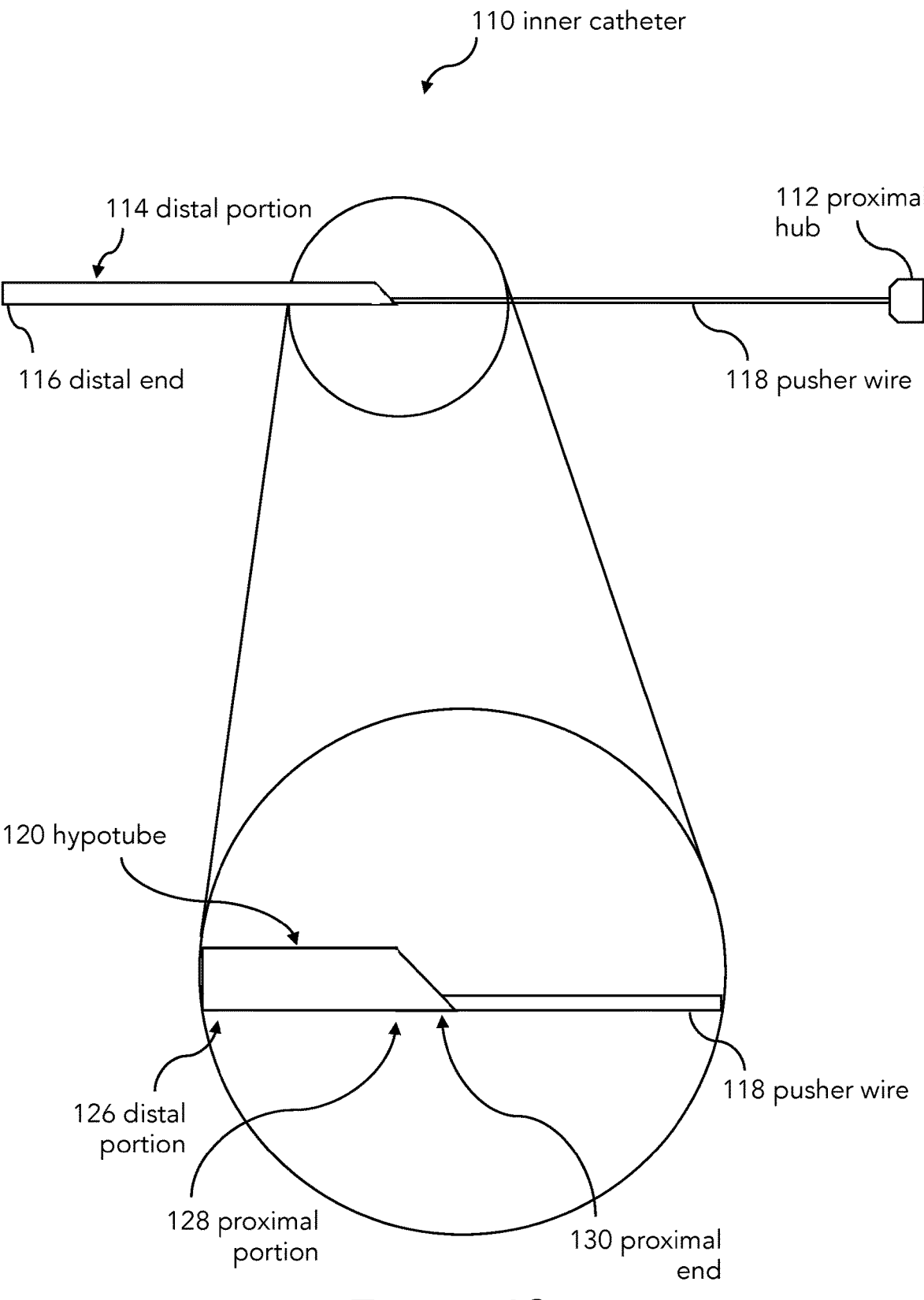
FIG. 10 illustrates an inner catheter including a hypotube, according to some embodiments.
Figure 11:
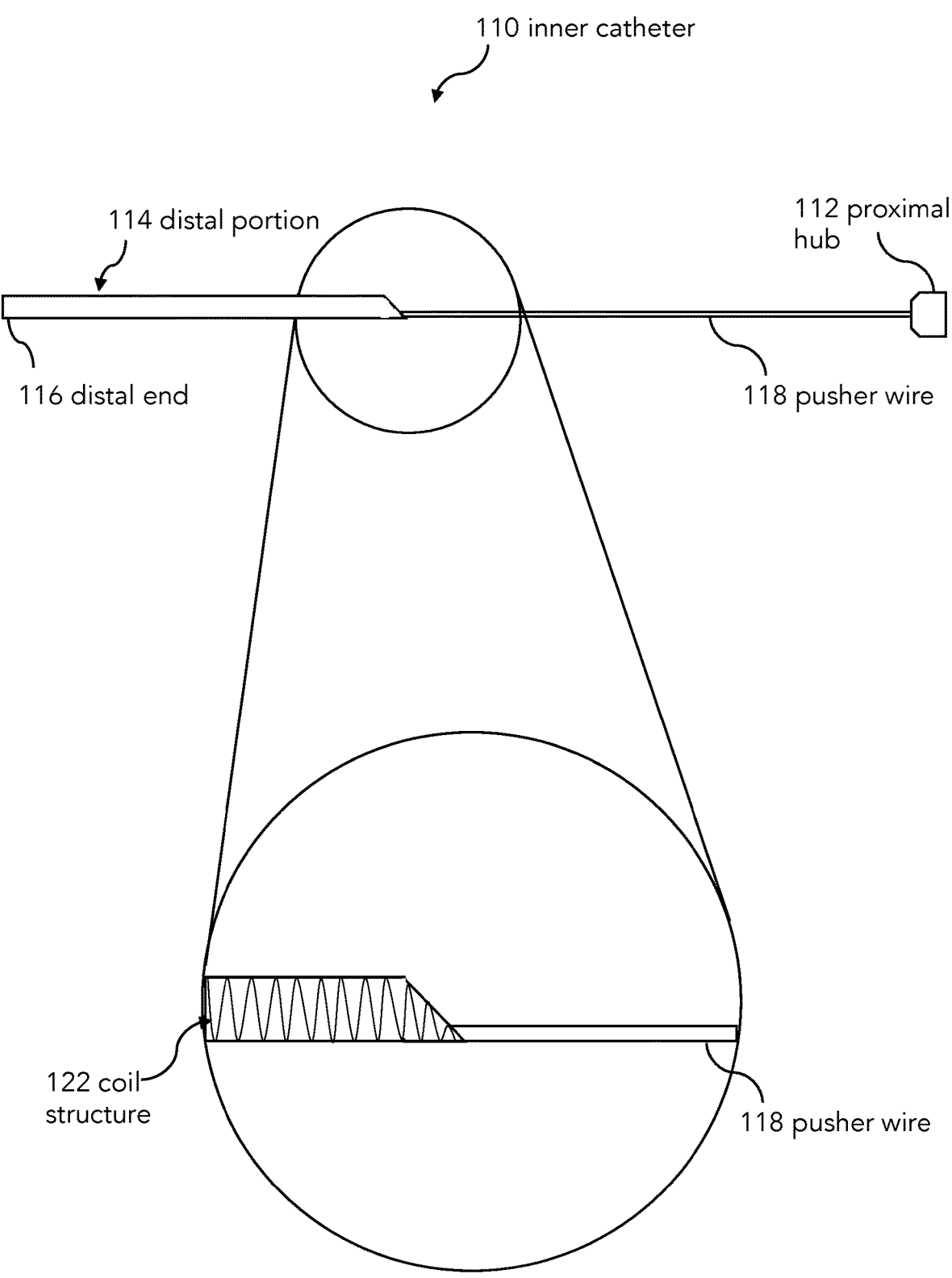
FIG. 11 illustrates an inner catheter including a coil structure, according to some embodiments.
Figure 12:
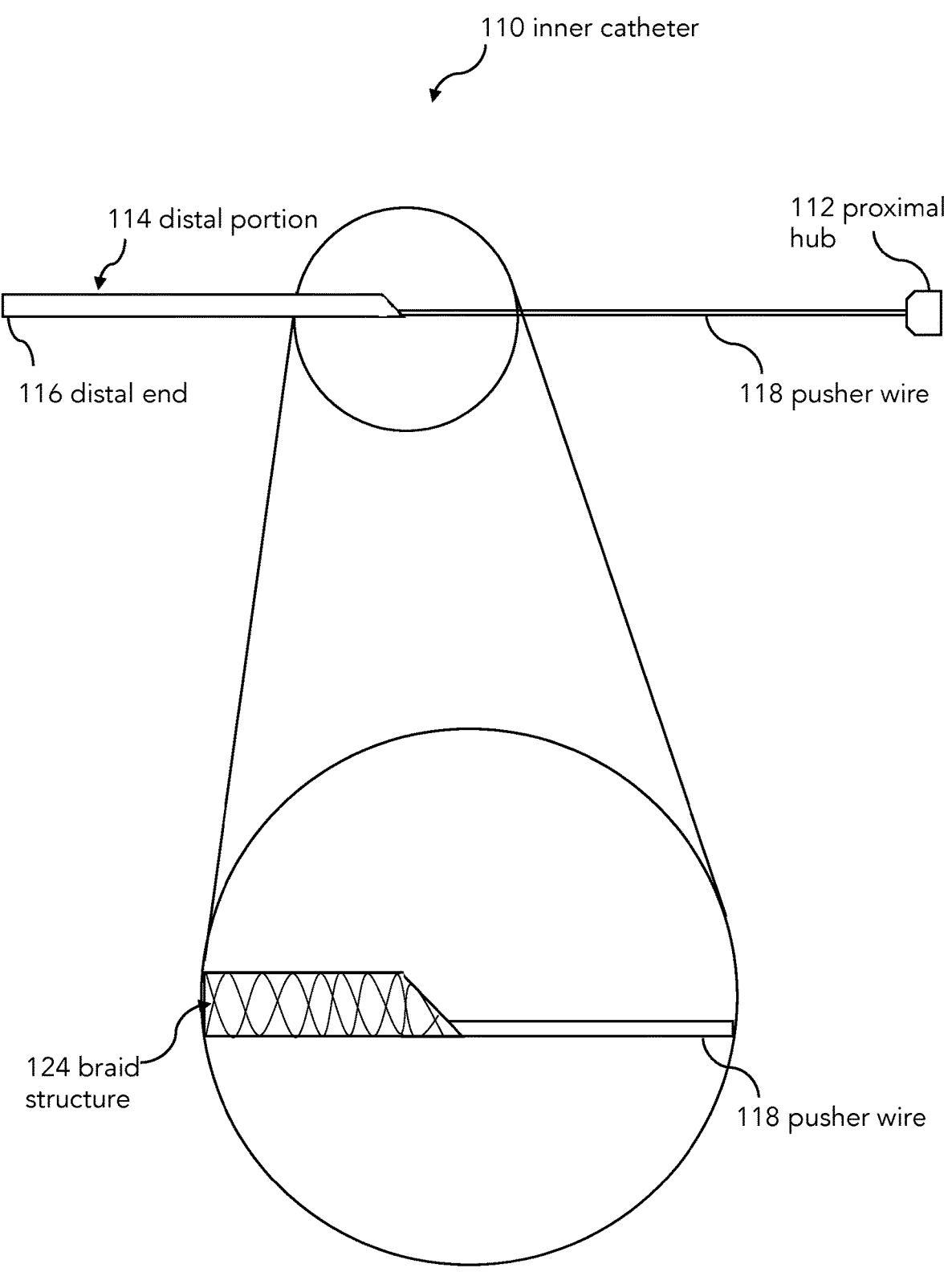
FIG. 12 illustrates an inner catheter including a braid structure, according to some embodiments.

FIGS. 10-12 illustrate the inner catheter 110, which, in some embodiments, comprises a proximal hub 112, a distal portion 114 having a distal end 116 located opposite the proximal hub 112, and a pusher wire 118 extending between the proximal hub 112 and the distal portion 114. As illustrated in the inset view of FIG. 10, the distal portion 114 may comprise a hypotube 120. In some embodiments, the hypotube 120 comprises a stainless steel hypotube. The hypotube 120 may comprise a nitinol hypotube. It should be noted that the hypotube 120 may be comprised of any suitable material, and, in some embodiments, is a laser-cut hypotube. In some embodiments, the hypotube 120 comprises a distal portion 126 and a proximal portion 128 located opposite the distal portion 126. As shown, the proximal portion 128 may be configured to taper to a proximal end 130 coupled to the pusher wire 118. Rather than a hypotube 120, the distal portion 114 of the inner catheter 110 may comprise a coil structure 122, as illustrated in FIG. 11, or a braid structure 124, as illustrated in FIG. 12. It should be noted that the distal portion 114 may comprise any suitable material configuration and is not limited to the examples shown in the Figures and discussed in this disclosure.

As shown in FIGS. 10-12, and due to the inclusion of the pusher wire 118, in some embodiments, the distal portion 114 of the inner catheter 110 defines a length substantially less than the full length of the inner catheter 110. In comparison, the outer catheter 102 shown in FIG. 9 may comprise a single tube defining substantially the full length of the outer catheter 102, minus the proximal end 104. Accordingly, in the catheter system 100, the outer catheter 102 may be considered a "full catheter" and the inner catheter 110 may be considered a "partial catheter." The distal portion 114 of the inner catheter 110, whether a hypotube 120, coil structure 122, or braid structure 124, may define a length of about twenty centimeters. In some embodiments, the distal portion 114 defines a length less than twenty centimeters. The distal portion 114 may define a length greater than twenty centimeters.

In some embodiments, the pusher wire 118 is fixedly coupled (e.g., via welding, adhesive, or the like) to the distal portion 114 of the inner catheter 110. The pusher wire 118 may be configured to facilitate navigation of the inner catheter 110 through the working lumen 108 of the outer catheter 102. For example, during a procedure, a physician (or another qualified medical professional) may be configured to "push" the inner catheter 110 through the outer catheter 102 using the proximal hub 112 and/or the pusher wire 118. The relative rigidity of the pusher wire 118 may help advance the inner catheter 110 with limited twisting, kinking, bending, etc. of the distal portion 114. In some embodiments, the pusher wire 118 comprises a round wire. The pusher wire 118 may comprise a flat wire.

Figure 13A:
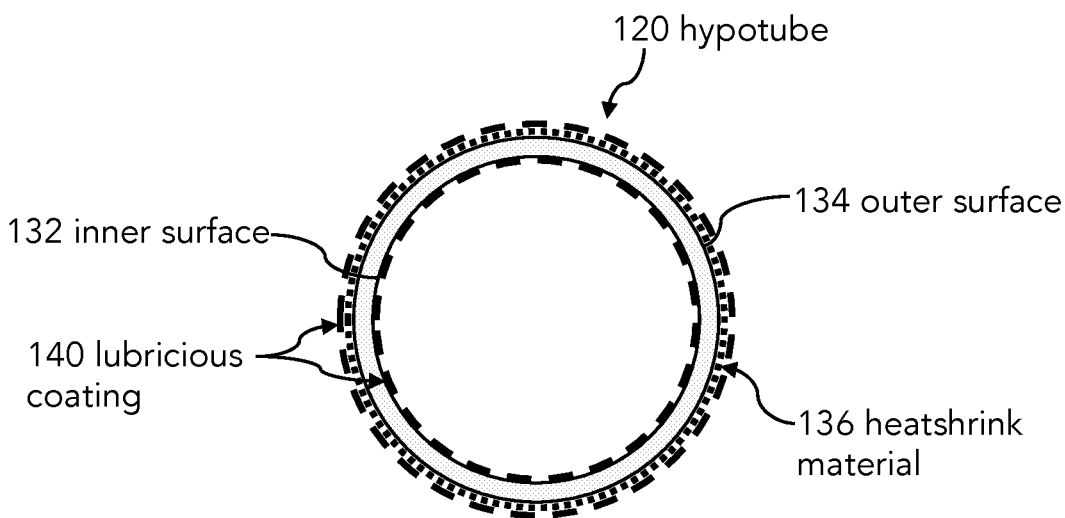
FIGS. 13A and 13B illustrate cross-sectional views of a hypotube, according to some embodiments.
Figure 13B:
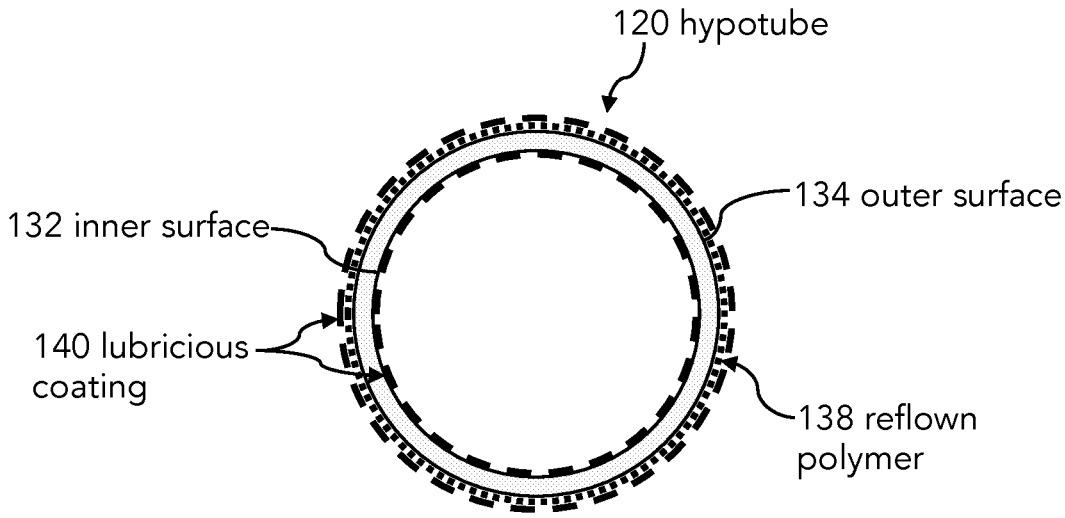

Turning now to FIGS. 13A and 13B, cross-sectional views of the hypotube 120 are shown. In some embodiments, the hypotube 120 comprises an inner surface 132 and an outer surface 134 located opposite the inner surface 132. The outer surface 134 may be covered in a heatshrink material 136, as shown in FIG. 13A. The heatshrink material 136 may comprise a material laminated or melted onto the outer surface 134 of the hypotube 120. In some embodiments, at least a portion of the heatshrink material 136 and at least a portion of the inner surface 132 of the hypotube 120 are coated with a lubricious coating 140. In some embodiments, substantially the entirety of the heatshrink material 136 and substantially the entirety of the inner surface 132 are coated with the lubricious coating 140. At least a portion of the heatshrink material 136 and substantially the entirety of the inner surface 132 may be coated with the lubricious coating 140. Alternatively, substantially the entirety of the heatshrink material 136 and at least a portion of the inner surface 132 may be coated with the lubricious coating 140.

The lubricious coating 140 may comprise a hydrophilic coating. In some embodiments, the lubricious coating 140 comprises silicone. The lubricious coating 140 may comprise any suitable type of coating, and is not intended to be limited to the examples discussed in this disclosure. In some embodiments, the lubricious coating 140 helps facilitate smooth navigation of the hypotube 120 through the working lumen 108 of the outer catheter 102. In an embodiment where the inner catheter 110 extends distally from the outer catheter 102, the lubricious coating 140 may also help facilitate smooth navigation of the hypotube 120 through a patient's vasculature. In some embodiments, the lubricious coating 140 on the inner surface 132 of the hypotube 120 facilitates smooth movement of a secondary device (e.g., a guidewire, microcatheter, specialized device, etc.) through the hypotube 120.

FIG. 13B illustrates that, in some embodiments, the outer surface 134 of the hypotube 120 is covered in a reflown polymer 138 rather than a heatshrink material 136. At least a portion of the reflown polymer 138 and at least a portion of the inner surface 132 of the hypotube 120 may be coated with the lubricious coating 140. In some embodiments, substantially the entirety of the reflown polymer 138 and substantially the entirety of the inner surface 132 of the hypotube 120 are coated with the lubricious coating 140. At least a portion of the reflown polymer 138 and substantially the entirety of the inner surface 132 may be coated with the lubricious coating 140. Alternatively, substantially the entirety of the reflown polymer 138 and at least a portion of the inner surface 132 may be coated with the lubricious coating 140.

The outer surface 134 of the hypotube 120 may be covered with a combination of the heatshrink material 136 and the reflown polymer 138. In some embodiments, at least a portion of the hypotube 120 includes a PTFE liner rather than the lubricious coating 140. For example, half of the hypotube 120 may include a PTFE liner while the other half includes the lubricious coating 140. Alternatively, half of the hypotube 120 may include a PTFE liner while the other half includes no lubricious coating 140. The hypotube 120 may also include neither a PTFE liner nor a lubricious coating 140. It should also be noted that embodiments of the catheter system 100 including the coil structure 122 or braid structure 124, as illustrated in FIGS. 11 and 12, respectively, may also include a heatshrink material 136, reflown polymer 138, or combination thereof to cover the coil structure 122 or braid structure 124, as applicable. In addition, embodiments with the coil structure 122 and/or braid structure 124 may include the lubricious coating 140 as illustrated in FIGS. 13A and 13B.

Figure 14:
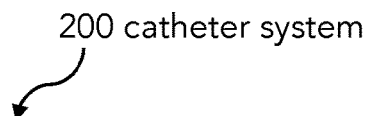
FIG. 14 illustrates a catheter system including an outer catheter and an inner catheter, according to some embodiments.
Figure 14:
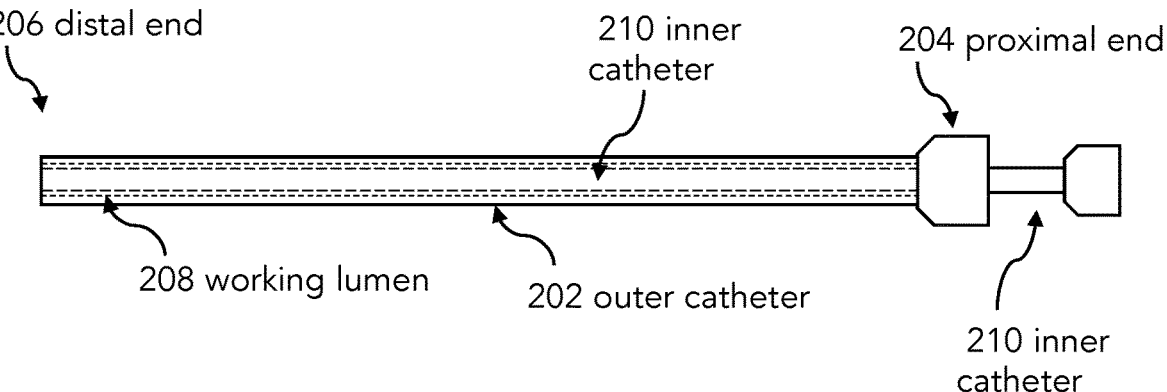

Referring now to FIG. 14, a catheter system 200 is shown. In some embodiments, the catheter system 200 comprises an outer catheter 202 having a proximal end 204, a distal end 206 located opposite the proximal end 204, and a working lumen 208 extending between the proximal end 204 and the distal end 206. The catheter system 200 may also include an inner catheter 210, and the working lumen 208 may be configured to at least partially receive the inner catheter 210, as demonstrated in FIG. 14.

Figure 15:
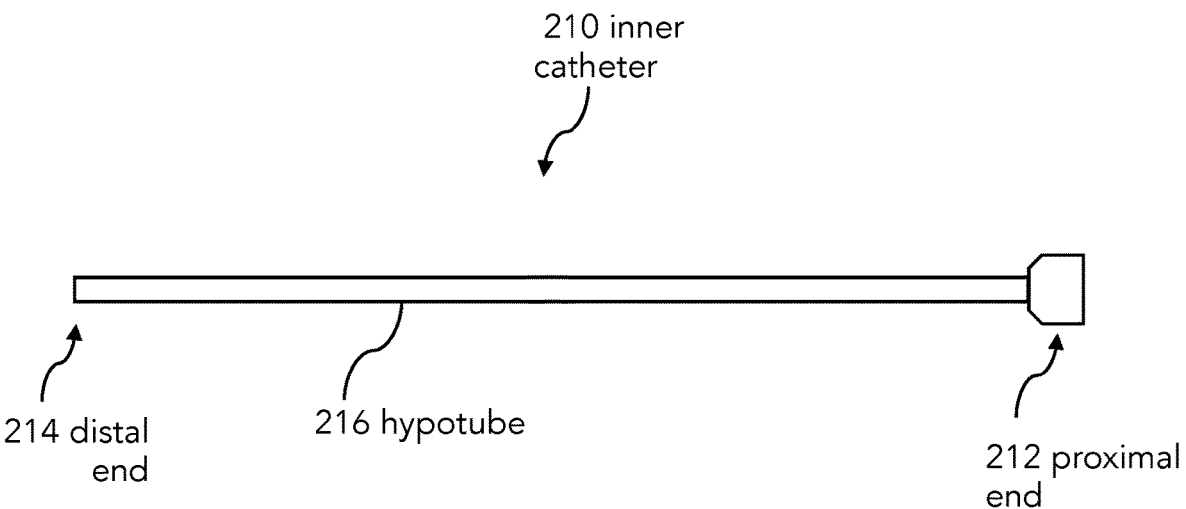
FIG. 15 illustrates an inner catheter comprising a hypotube, according to some embodiments.

FIG. 15 illustrates the inner catheter 210 in more detail, including the proximal end 212 and the distal end 214 located opposite the proximal end 212. Unlike the inner catheter 110 of the catheter system 100 (shown in FIGS. 9-13), the inner catheter 210 may comprise a "full" catheter rather than a "partial" catheter. Stated differently, the inner catheter 210 may comprise a hypotube 216 configured to extend the full length from the proximal end 212 to the distal end 214. Similar to the hypotube 120 of the inner catheter 110, the hypotube 216 of the inner catheter 210 may comprise a laser-cut hypotube. In some embodiments, the hypotube 216 comprises a stainless steel hypotube. The hypotube 216 may comprise a nitinol hypotube, or a hypotube constructed of any other suitable material.

Figure 16A:
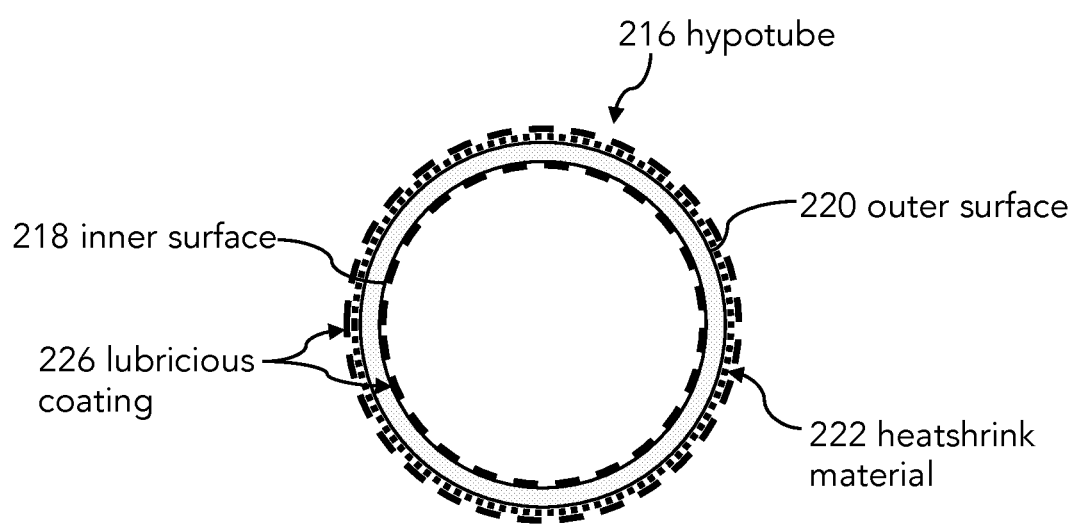
FIGS. 16A and 16B illustrate cross-sectional views of a hypotube, according to some embodiments.
Figure 16B:
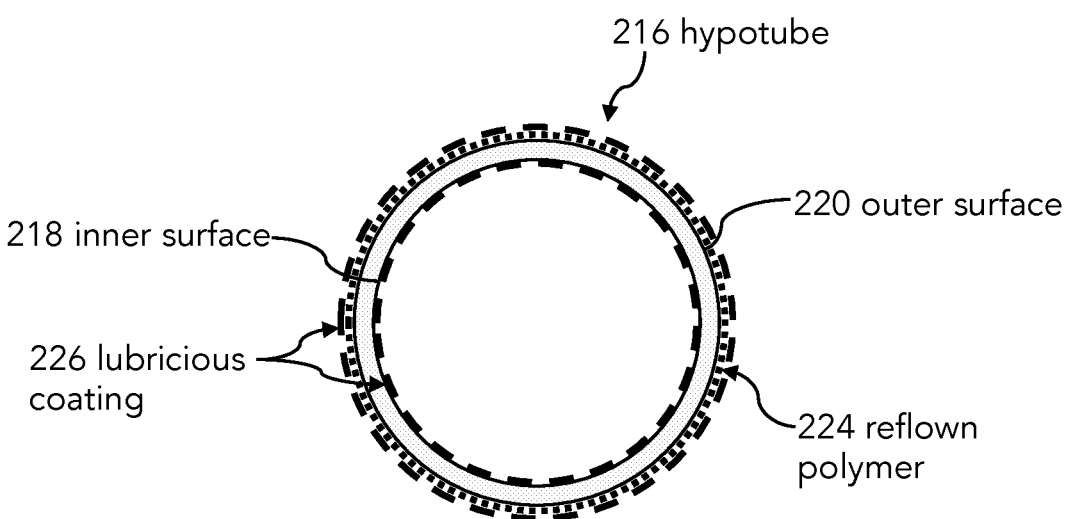

FIGS. 16A and 16B are similar to FIGS. 13A and 13B, though they illustrate the hypotube 216 rather than the hypotube 120. FIGS. 16A and 16B show cross-sectional views of the hypotube 216, wherein the hypotube 216 comprises an inner surface 218 and an outer surface 220 located opposite the inner surface 218. The outer surface 220 may be covered in a heatshrink material 222, as shown in FIG. 16A. The heatshrink material 222 may comprise a material laminated or melted onto the outer surface 220 of the hypotube 216. In some embodiments, at least a portion of the heatshrink material 222 and at least a portion of the inner surface 218 of the hypotube 216 are coated with a lubricious coating 226. In some embodiments, substantially the entirety of the heatshrink material 222 and substantially the entirety of the inner surface 218 are coated with the lubricious coating 226. At least a portion of the heatshrink material 222 and substantially the entirety of the inner surface 218 may be coated with the lubricious coating 226. Alternatively, substantially the entirety of the heatshrink material 222 and at least a portion of the inner surface 218 may be coated with the lubricious coating 226.

In some embodiments, the lubricious coating 226 is substantially similar to the lubricious coating 140 of the catheter system 100. The lubricious coating 226 may comprise a hydrophilic coating. In some embodiments, the lubricious coating 226 comprises silicone. The lubricious coating 226 may comprise any suitable type of coating, and is not intended to be limited to the examples discussed in this disclosure. In some embodiments, the lubricious coating 226 helps facilitate smooth navigation of the hypotube 216 through the working lumen 208 of the outer catheter 202. In an embodiment where the inner catheter 210 extends distally from the outer catheter 202, the lubricious coating 226 may also help facilitate smooth navigation of the hypotube 216 through a patient's vasculature. In some embodiments, the lubricious coating 226 on the inner surface 218 of the hypotube 216 facilitates smooth movement of a secondary device (e.g., a guidewire, microcatheter, specialized device, etc.) through the hypotube 216.

FIG. 16B illustrates that, in some embodiments, the outer surface 220 of the hypotube 216 is covered in a reflown polymer 224 rather than a heatshrink material 222. At least a portion of the reflown polymer 224 and at least a portion of the inner surface 218 of the hypotube 216 may be coated with the lubricious coating 226. In some embodiments, substantially the entirety of the reflown polymer 224 and substantially the entirety of the inner surface 218 of the hypotube 216 are coated with the lubricious coating 226. At least a portion of the reflown polymer 224 and substantially the entirety of the inner surface 218 may be coated with the lubricious coating 226. Alternatively, substantially the entirety of the reflown polymer 224 and at least a portion of the inner surface 218 may be coated with the lubricious coating 226.

The outer surface 220 of the hypotube 216 may be covered with a combination of the heatshrink material 222 and the reflown polymer 224. In some embodiments, at least a portion of the hypotube 216 includes a PTFE liner rather than the lubricious coating 226. For example, half of the hypotube 216 may include a PTFE liner while the other half includes the lubricious coating 226. Alternatively, half of the hypotube 216 may include a PTFE liner while the other half includes no lubricious coating 226. The hypotube 216 may also include neither a PTFE liner nor a lubricious coating 226. It should also be noted that the inner catheter 210 may comprise, rather than the hypotube 216, a coil structure or braid structure, similar to those illustrated in FIGS. 11 and 12, respectively. In some embodiments, the inner catheter 210 comprising a coil and/or braid structure also includes a heatshrink material 222, reflown polymer 224, or combination thereof to cover the coil structure and/or braid structure, as applicable. In addition, embodiments with the coil structure and/or braid structure may include the lubricious coating 226 as illustrated in FIGS. 16A and 16B.

Figure 17:
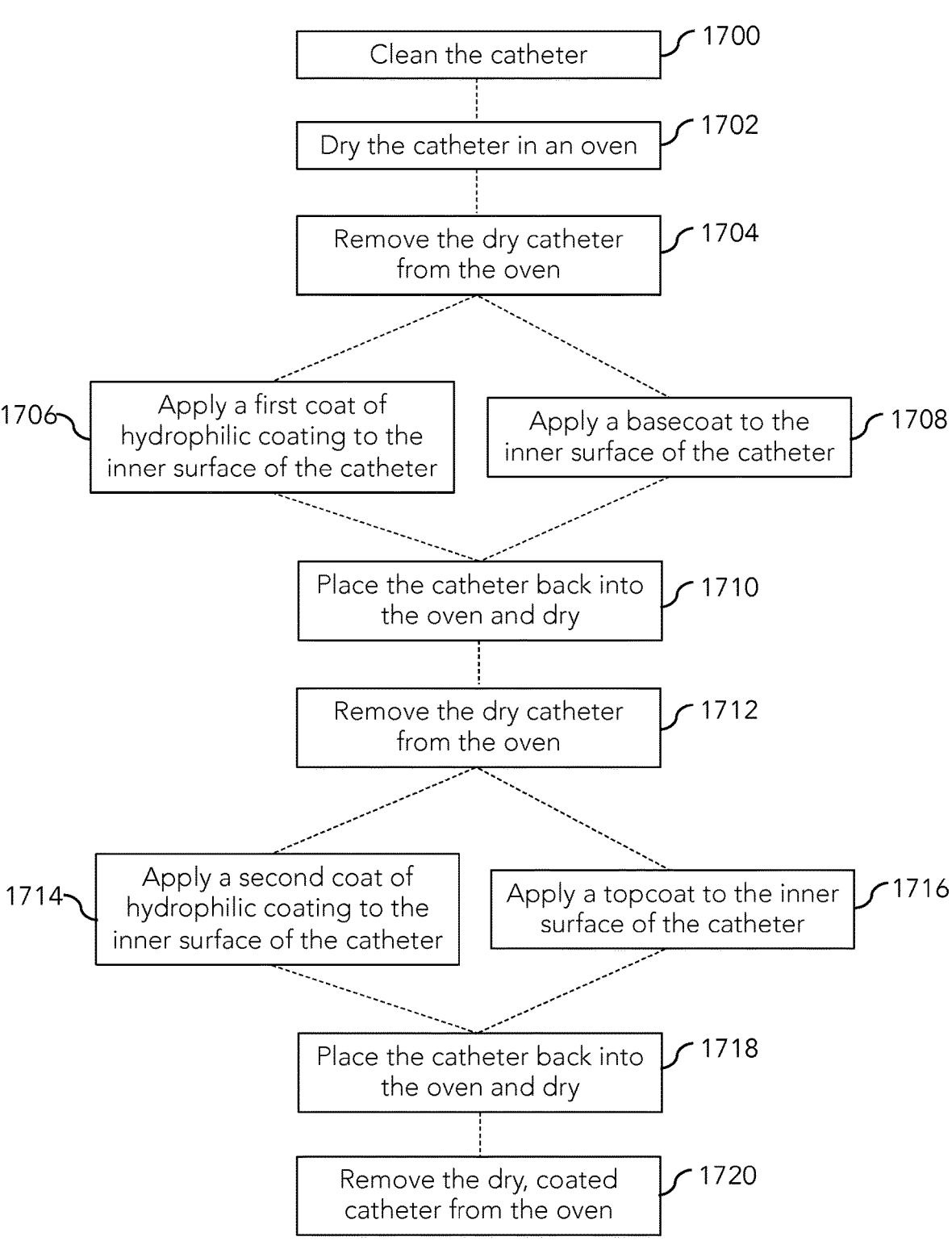
FIGS. 17 and 18 illustrate flow charts explaining the processes of applying hydrophilic coatings, according to some embodiments.

FIG. 17 includes a flowchart illustrating a process of coating and curing an inner surface of a catheter. For the purposes of this disclosure, the "catheter" recited in FIG. 17 may comprise elements of the catheter system 10 (i.e., the outer catheter 12 or the inner catheter 26), elements of the catheter system 100 (i.e., the outer catheter 102 or the inner catheter 110), and/or elements of the catheter system 200 (i.e., the outer catheter 202 or the inner catheter 210). The steps of the process should be considered as applying to any of the catheters recited in this disclosure.

The process shown in FIG. 17 starts with cleaning the catheter, at step 1700. In some embodiments, cleaning the catheter includes flushing the catheter with purified water, isopropyl alcohol ("IPA"), a mix of IPA and water, or some other suitable cleansing fluid. The next step is to dry the catheter in an oven, at step 1702. The drying step may include placing the clean catheter in an oven set to a temperature between 0° C. and 400° C. and applying positive or negative pressured air (e.g., oxygen, a mix of oxygen and nitrogen, etc.) to the hub of the catheter in order to dry the inner surface of the catheter. The process continues with step 1704: remove the dry catheter from the oven.

Next, the process can continue in one of two possible steps. One option is to apply a first coat of hydrophilic coating to the inner surface of the catheter, shown at step 1706. Alternatively, a basecoat may be applied to the inner surface of the catheter, at step 1708. Both steps 1706 and 1708 may use positive or negative pressure to fill the catheter with either the hydrophilic coating (step 1706) or the basecoat (step 1708). The catheter may be filled with the relevant coating material from either end of the catheter body. In some embodiments, the relevant coating material substantially continuously flows through the catheter for a predetermined amount of time to ensure an adequate amount of coating is applied. The relevant coating material may dwell within the catheter, rather than flow through, for a predetermined amount of time.

After either step 1706 or step 1708, the process may continue to place the catheter back into the oven to dry, at step 1710. Similar to the first drying step (i.e., step 1702), step 1710 may involve placing the clean catheter in an oven set to a temperature between 0° C. and 400° C. and applying positive or negative pressured air (e.g., oxygen, a mix of oxygen and nitrogen, etc.) to the hub of the catheter in order to dry the inner surface of the catheter. Step 1710 may be considered a "heat curing" step, as heat is used to dry (i.e., cure) the coating. Next, the positive or negative pressure source is disconnected and the dry catheter is removed from the oven, at step 1712.

At this point, the process again diverges into two different options. One is to apply a second coat of hydrophilic coating to the inner surface of the catheter, at step 1714. The other is to apply a topcoat to the inner surface of the catheter, at step 1716. Similar to the application of the first coat of hydrophilic coating (at step 1706) and the application of the basecoat (at step 1708), both steps 1714 and 1716 may use positive or negative pressure to fill the catheter with the relevant coating material from either end of the catheter body. In some embodiments, the relevant coating material substantially continuously flows through the catheter for a predetermined amount of time to ensure an adequate amount of coating is applied. The relevant coating material may dwell within the catheter, rather than flow through, for a predetermined amount of time.

Next, the process continues with placing the catheter back into the oven to dry (or "heat cure") again, at step 1718. Like the first and second drying steps (step 1702 and step 1710), step 1718 may involve placing the catheter in an oven set to a temperature between 0° C. and 400° C. and applying positive or negative pressured air (e.g., oxygen, a mix of oxygen and nitrogen, etc.) to the hub of the catheter in order to dry the inner surface of the catheter. The process concludes by disconnecting the positive or negative pressure source and removing the dry, coated catheter from the oven, at step 1720.

Figure 18:
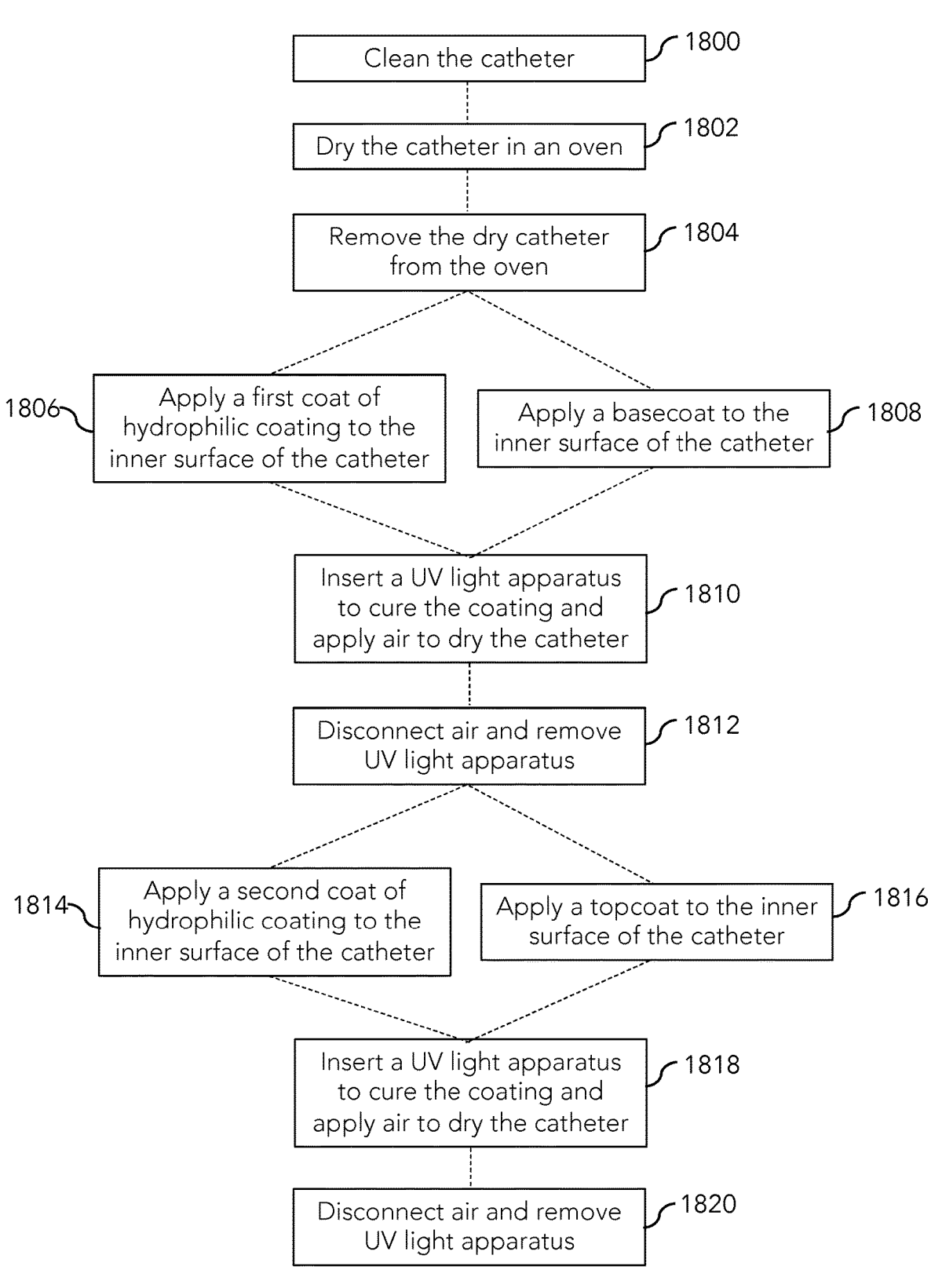

FIG. 18 is similar to FIG. 17, and includes a flowchart illustrating a slightly different process of coating and curing an inner surface of a catheter. As with the process shown in FIG. 17, for the purposes of this disclosure, the "catheter" recited in FIG. 18 may comprise elements of the catheter system 10 (i.e., the outer catheter 12 or the inner catheter 26), elements of the catheter system 100 (i.e., the outer catheter 102 or the inner catheter 110), and/or elements of the catheter system 200 (i.e., the outer catheter 202 or the inner catheter 210). The steps of the process should be considered as applying to any of the catheters recited in this disclosure.

The process shown in FIG. 18 starts with cleaning the catheter, at step 1800. In some embodiments, cleaning the catheter includes flushing the catheter with purified water, IPA, a mix of IPA and water, or some other suitable cleansing fluid. The next step is to dry the catheter in an oven, at step 1802. The drying step may include placing the clean catheter in an oven set to a temperature between 0° C. and 400° C. and applying positive or negative pressured air (e.g., oxygen, a mix of oxygen and nitrogen, etc.) to the hub of the catheter in order to dry the inner surface of the catheter. The process continues with step 1804: remove the dry catheter from the oven.

Next, the process can continue in one of two possible steps. One option is to apply a first coat of hydrophilic coating to the inner surface of the catheter, shown at step 1806. Alternatively, a basecoat may be applied to the inner surface of the catheter, at step 1808. Both steps 1806 and 1808 may use positive or negative pressure to fill the catheter with either the hydrophilic coating (step 1806) or the basecoat (step 1808). The catheter may be filled with the relevant coating material from either end of the catheter body. In some embodiments, the relevant coating material substantially continuously flows through the catheter for a predetermined amount of time to ensure an adequate amount of coating is applied. The relevant coating material may dwell within the catheter, rather than flow through, for a predetermined amount of time.

After either step 1806 or step 1808, the process may continue by inserting a UV light apparatus to cure the coating and applying positive or negative pressured air (e.g., oxygen, a mix of oxygen and nitrogen, etc.) to the hub of the catheter in order to dry the inner surface of the catheter, at step 1810. In some embodiments, the UV light apparatus is inserted into the inner diameter of the catheter to cure the coating on the inner surface. Next, the positive or negative pressure source is disconnected and the UV light apparatus is removed from the catheter, at step 1812.

At this point, the process again diverges into two different options. One is to apply a second coat of hydrophilic coating to the inner surface of the catheter, at step 1814. The other is to apply a topcoat to the inner surface of the catheter, at step 1816. Similar to the application of the first coat of hydrophilic coating (at step 1806) and the application of the basecoat (at step 1808), both steps 1814 and 1816 may use positive or negative pressure to fill the catheter with the relevant coating material from either end of the catheter body. In some embodiments, the relevant coating material substantially continuously flows through the catheter for a predetermined amount of time to ensure an adequate amount of coating is applied. The relevant coating material may dwell within the catheter, rather than flow through, for a predetermined amount of time.

Next, the process continues with another round of UV light curing, at step 1818. Like the first UV curing step (step 1810), step 1818 may involve inserting a UV light apparatus to cure the coating and applying positive or negative pressured air (e.g., oxygen, a mix of oxygen and nitrogen, etc.) to the hub of the catheter in order to dry the inner surface of the catheter. The UV light apparatus may be inserted into the inner diameter of the catheter to cure the coating on the inner surface. The process concludes by disconnecting the positive or negative pressure source and removing the UV light apparatus from the catheter, at step 1820.

It should be noted that the catheter system 10 may be configured for use in various procedures conducted in a variety of locations of a patient's anatomy. Though brain-specific thrombectomy is discussed, the disclosure should not be considered limiting to any specific type or location of the procedure. The catheter system 10 may be used for the aspiration of clots throughout a patient's body, and the various aspects of the catheter system 10 discussed above may improve the rate of clot removal in a number of procedure locations.

Catheter systems may include a full outer catheter 102 and partial inner catheter 110, like the catheter system 100, or may include a full outer catheter 202 and a full inner catheter 210, like the catheter system 200. In some embodiments, a catheter system includes a partial outer catheter and a full inner catheter. A catheter system may also include a partial outer catheter and a partial inner catheter.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are non-limiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

To increase the clarity of various features, other features are not labeled in each figure.

The various features and processes described above may be used independently of one another, or may be combined in various ways. All possible combinations and sub-combinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "substantially" is used to mean "completely" or "nearly completely." For example, the disclosure includes, "the first hydrophilic coating comprises a substantially smooth surface." In this context, "substantially" is used to mean that the first hydrophilic coating may comprise a completely or nearly completely smooth surface.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A catheter system, comprising:
an outer catheter having a proximal end, a distal end located opposite the proximal end, a working lumen extending between the proximal end and the distal end, an outer surface defining an outer diameter, and an inner surface defining an inner diameter;
an inner catheter having a proximal end, a distal end located opposite the proximal end, a working lumen extending between the proximal end and the distal end, an outer surface defining an outer diameter, and an inner surface defining an inner diameter, wherein the working lumen of the outer catheter is configured to at least partially receive the inner catheter;
a first hydrophilic coating located on the outer surface of the outer catheter, the first hydrophilic coating configured to reduce surface friction and increase lubricity between the outer surface of the outer catheter and a vessel wall, the first hydrophilic coating comprising a substantially smooth surface;
a second hydrophilic coating located on the inner surface of the outer catheter, the second hydrophilic coating configured to reduce surface friction and increase lubricity between the inner surface of the outer catheter and the outer surface of the inner catheter, the second hydrophilic coating comprising a textured surface;
a third hydrophilic coating located on the outer surface of the inner catheter, the third hydrophilic coating configured to reduce surface friction and increase lubricity between the inner surface of the outer catheter and the outer surface of the inner catheter, the third hydrophilic coating comprising a substantially smooth surface; and
a fourth hydrophilic coating located on the inner surface of the inner catheter, the fourth hydrophilic coating configured to reduce surface friction and increase lubricity on the inner surface of the inner catheter, the fourth hydrophilic coating comprising a textured surface.

2. The catheter system of claim 1, wherein the outer catheter comprises a device wall and the inner catheter comprises a device wall, wherein the device wall of the outer catheter includes at least one polymer coupled to an outer catheter reinforcement structure, and wherein the device wall of the inner catheter includes at least one polymer coupled to an inner catheter reinforcement structure.

3. The catheter system of claim 2, wherein the outer catheter reinforcement structure comprises a braid and coil reinforcement structure, and the inner catheter reinforcement structure comprises a braid and coil reinforcement structure.

4. The catheter system of claim 3, wherein the at least one polymer is configured to provide at least one of flexibility and structural support to the outer catheter and the inner catheter.

5. The catheter system of claim 4, wherein the braid and coil reinforcement structure comprises a coil defining a pitch smaller than 0.03 inches.

6. The catheter system of claim 2, wherein the device wall of the outer catheter is located between the first hydrophilic coating and the second hydrophilic coating, and wherein the device wall of the inner catheter is located between the third hydrophilic coating and the fourth hydrophilic coating.

7. The catheter system of claim 1, further comprising a guidewire configured to extend through the inner catheter, wherein the fourth hydrophilic coating is configured to reduce surface friction and increase lubricity between the guidewire and the inner surface of the inner catheter.

8. The catheter system of claim 1, wherein the first hydrophilic coating extends between the proximal end and the distal end of the outer catheter.

9. The catheter system of claim 1, wherein the first hydrophilic coating extends along a surface extending between the proximal end and the distal end of the outer catheter.

10. The catheter system of claim 1, wherein the second hydrophilic coating extends between the proximal end and the distal end of the outer catheter.

11. The catheter system of claim 1, wherein the second hydrophilic coating extends along a surface extending between the proximal end and the distal end of the outer catheter.

12. The catheter system of claim 1, wherein the third hydrophilic coating extends between the proximal end and the distal end of the inner catheter.

13. The catheter system of claim 1, wherein the third hydrophilic coating extends along a surface extending between the proximal end and the distal end of the euter inner catheter.

14. The catheter system of claim 1, wherein the fourth hydrophilic coating extends between the proximal end and the distal end of the inner catheter.

15. The catheter system of claim 1, wherein the first hydrophilic coating extends along a surface extending between the proximal end and the distal end of the outer catheter.

16. The catheter system of claim 1, further comprising:
an outer reinforcement structure located on the second hydrophilic coating, the outer reinforcement structure configured to provide structural support to the outer catheter; and
an inner reinforcement structure located on the fourth hydrophilic coating, the inner reinforcement structure configured to provide structural support to the inner catheter.

17. The catheter system of claim 16, wherein the outer reinforcement structure comprises a braid and coil reinforcement structure, and the inner reinforcement structure comprises a braid and coil reinforcement structure.

18. The catheter system of claim 16, further comprising:
an outer jacket structure coupled to the outer reinforcement structure, wherein the outer jacket structure is configured to provide at least one of flexibility and structural support to the outer catheter; and
an inner jacket structure coupled to the inner reinforcement structure, wherein the inner jacket structure is configured to provide at least one of flexibility and structural support to the inner catheter.

19. The catheter system of claim 18, wherein the outer jacket structure comprises a polymer jacket structure, and the inner jacket structure comprises a polymer jacket structure.

20. The catheter system of claim 16, further comprising:
an outer jacket structure coupled to the outer reinforcement structure, wherein the outer jacket structure is configured to cover the outer reinforcement structure and provide the substantially smooth surface; and
an inner jacket structure coupled to the inner reinforcement structure, wherein the inner jacket structure is configured to cover the inner reinforcement structure provide the textured surface.

* * * * *